(12) United States Patent
O'Quinn et al.

(10) Patent No.: US 7,618,428 B2
(45) Date of Patent: Nov. 17, 2009

(54) ENDOSCOPIC ROTARY ABRADER

(75) Inventors: Philip S. O'Quinn, Naples, FL (US);
Randall L. Hacker, Naples, FL (US);
Christine Bickenbach, Naples, FL (US);
Gerald Goldsmith, Naples, FL (US);
Robert A. Van Wyk, Largo, FL (US);
Gary R. Heisler, Middletown, CT (US)

(73) Assignee: Arthrex, Inc., Naples, FL (US)

( * ) Notice: Subject to any disclaimer, the term of this patent is extended or adjusted under 35 U.S.C. 154(b) by 470 days.

(21) Appl. No.: 11/365,939

(22) Filed: Mar. 2, 2006

(65) Prior Publication Data

US 2006/0217751 A1    Sep. 28, 2006

Related U.S. Application Data

(60) Provisional application No. 60/657,418, filed on Mar. 2, 2005.

(51) Int. Cl.
*A61B 17/22* (2006.01)
(52) U.S. Cl. ...................................... 606/159
(58) Field of Classification Search ................ 606/159, 606/167, 169, 170, 180; 604/22, 35, 67, 604/131, 155
See application file for complete search history.

(56) References Cited

U.S. PATENT DOCUMENTS

| 4,842,578 | A | | 6/1989 | Johnson et al. |
| 5,312,399 | A | | 5/1994 | Hakky et al. |
| 5,913,867 | A | * | 6/1999 | Dion .......................... 606/180 |
| 6,053,923 | A | * | 4/2000 | Veca et al. .................... 606/80 |
| 6,565,587 | B1 | * | 5/2003 | Heckele et al. .............. 606/167 |
| 6,638,289 | B1 | * | 10/2003 | Johnson et al. ............. 606/170 |
| 7,118,574 | B2 | * | 10/2006 | Patel et al. .................... 606/80 |
| 2003/0083681 | A1 | | 5/2003 | Moutafis et al. |
| 2004/0181251 | A1 | | 9/2004 | Hacker et al. |

FOREIGN PATENT DOCUMENTS

DE     38 28 478    5/1989
EP     0 199 041    10/1986

* cited by examiner

*Primary Examiner*—Anhtuan T Nguyen
*Assistant Examiner*—Jocelin C Tanner
(74) *Attorney, Agent, or Firm*—Dickstein Shapiro LLP

(57) ABSTRACT

An endoscopic rotary abrader allowing for increased burr size while maintaining the required minimum clearance between the burr and the hood. This is accomplished either by an offset configuration of non-concentric inner and outer tubes, where the inner tube is shifted laterally away from the hood, or by employing an enlarged hood.

20 Claims, 40 Drawing Sheets

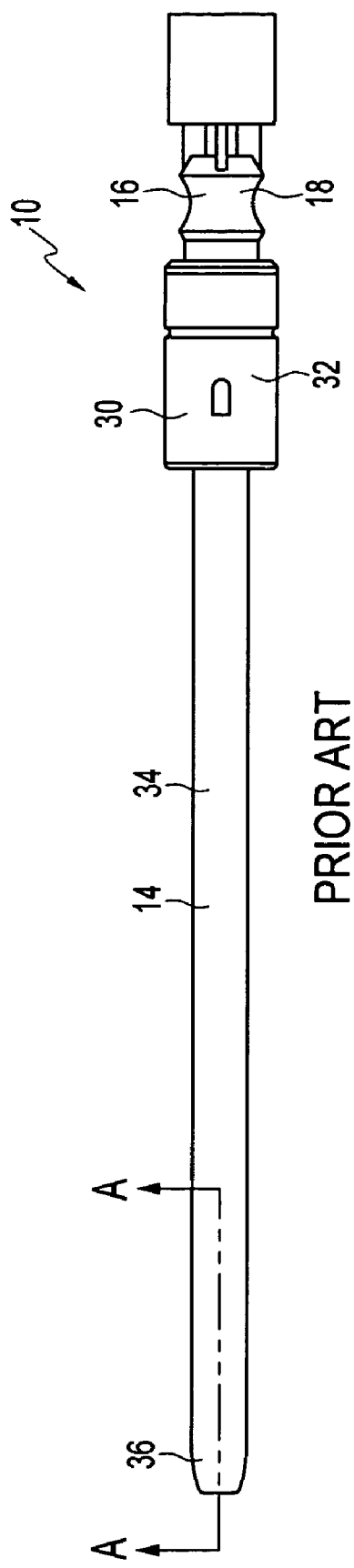
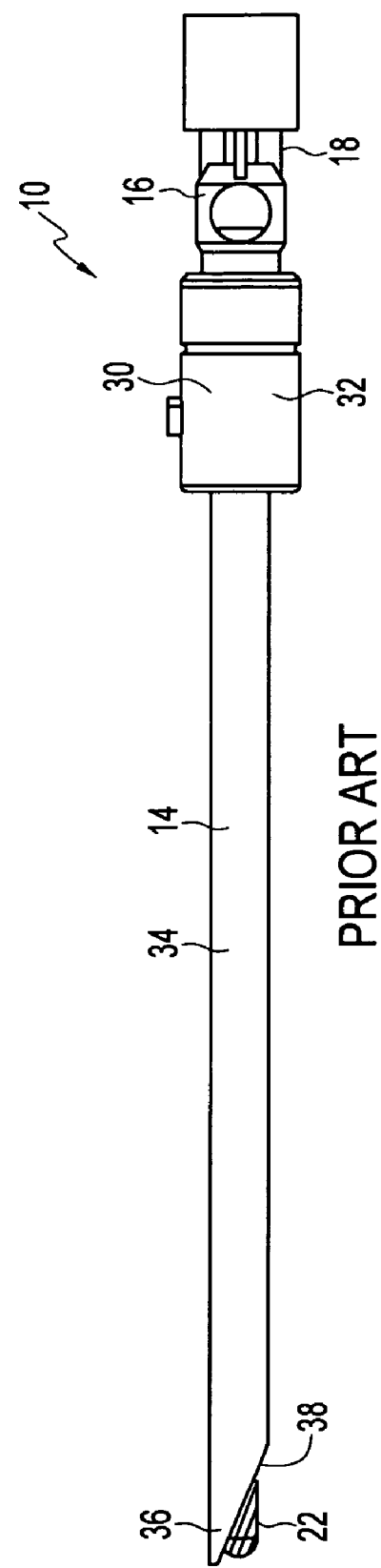
PRIOR ART
FIG. 2
PRIOR ART
FIG. 3

SECTION A-A

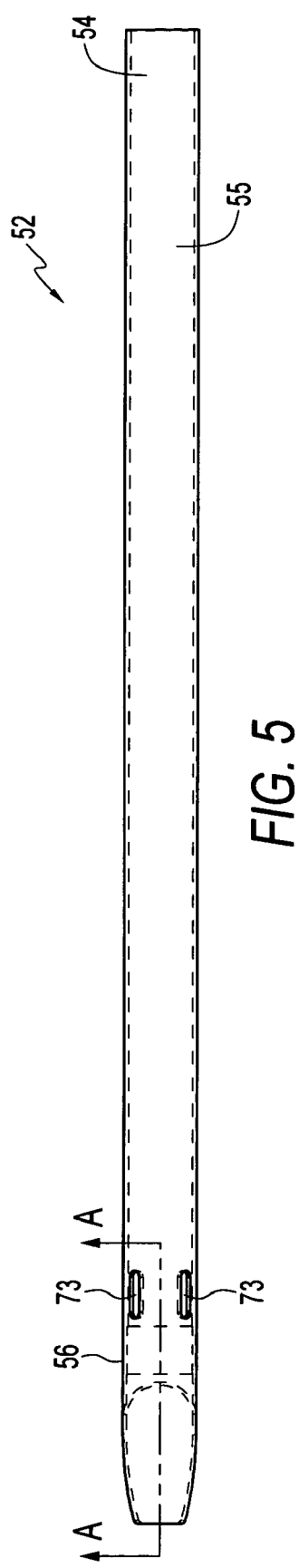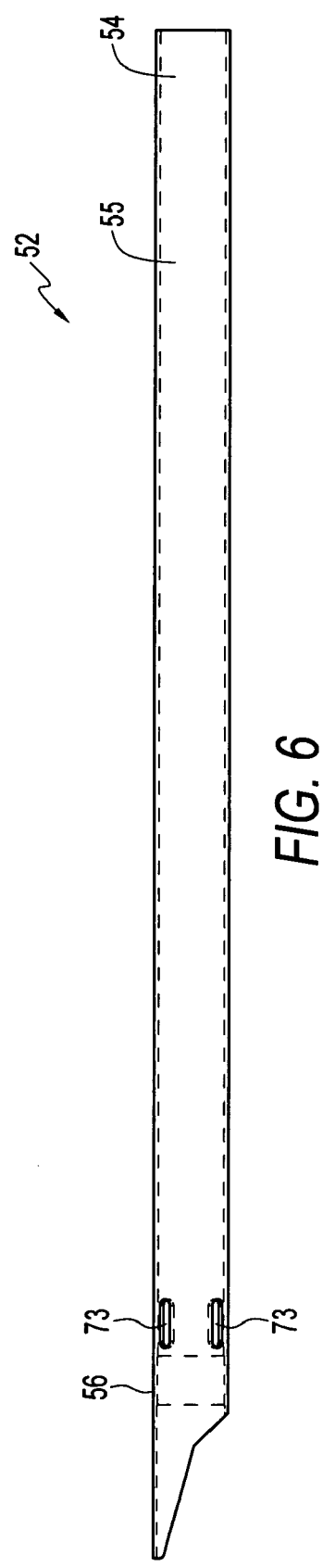
FIG. 5
FIG. 6

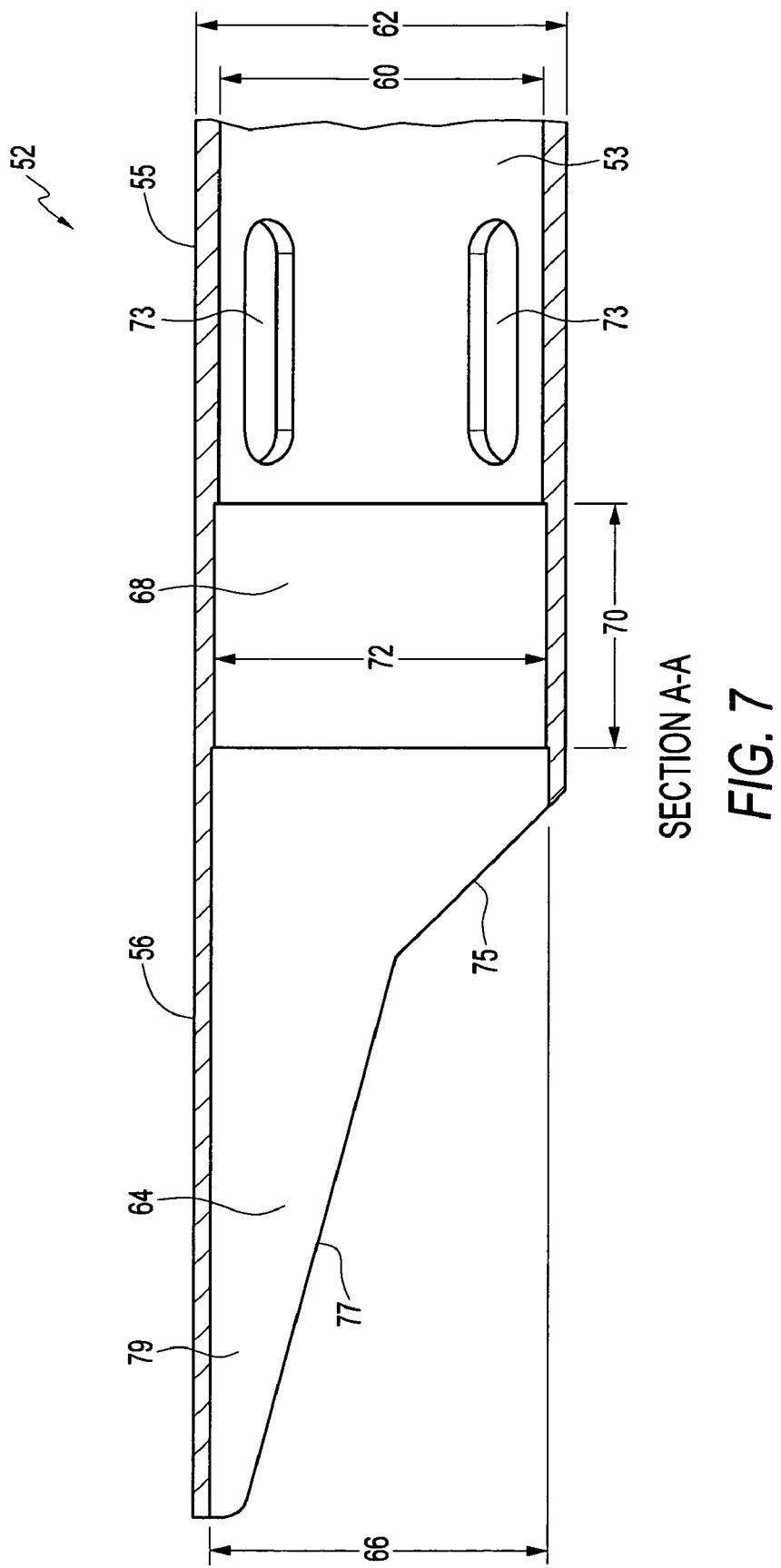
FIG. 7 SECTION A-A

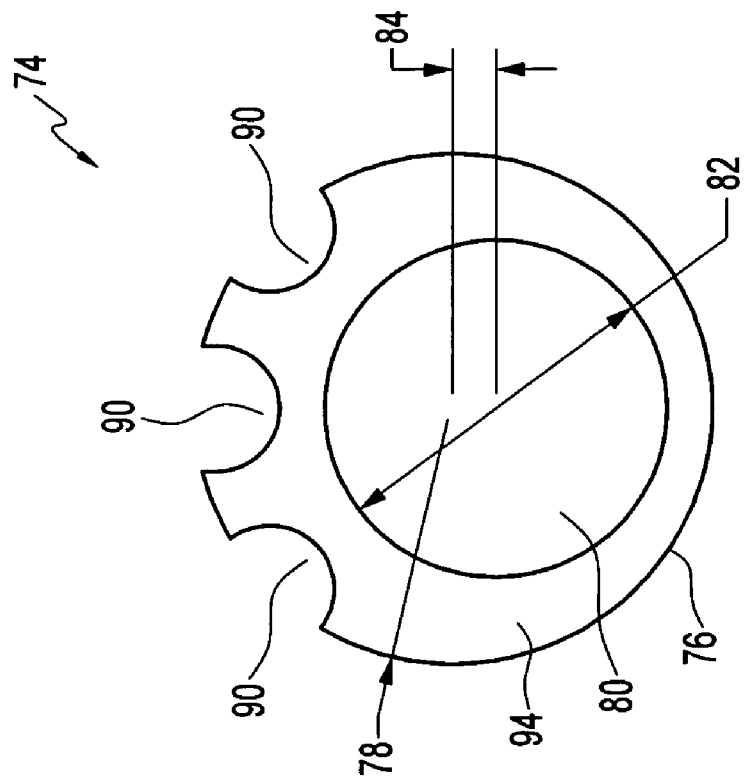
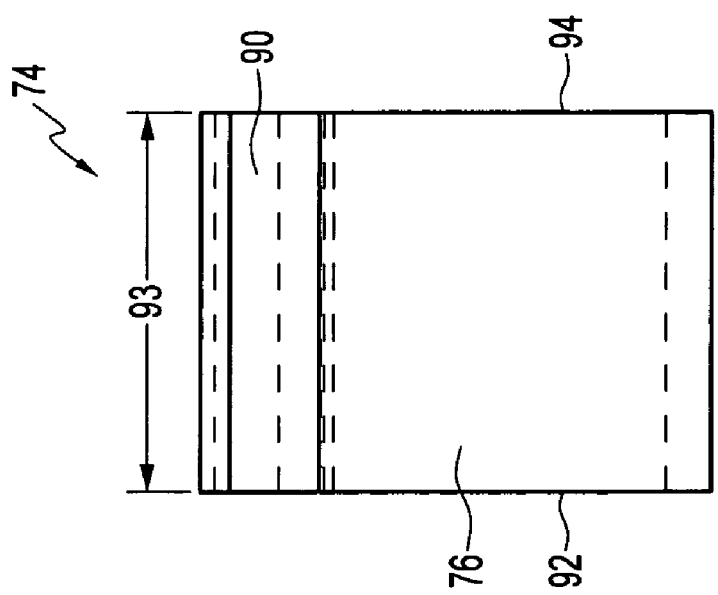

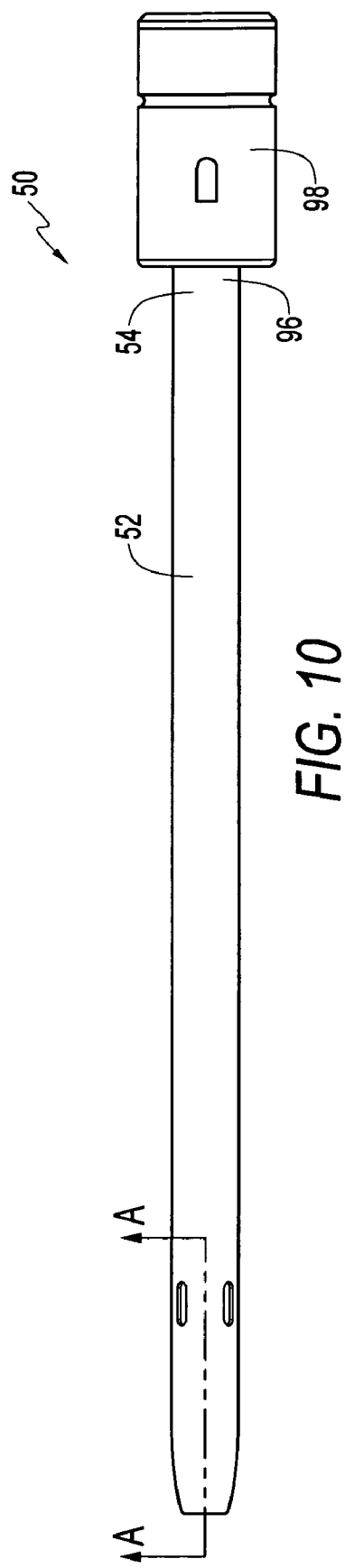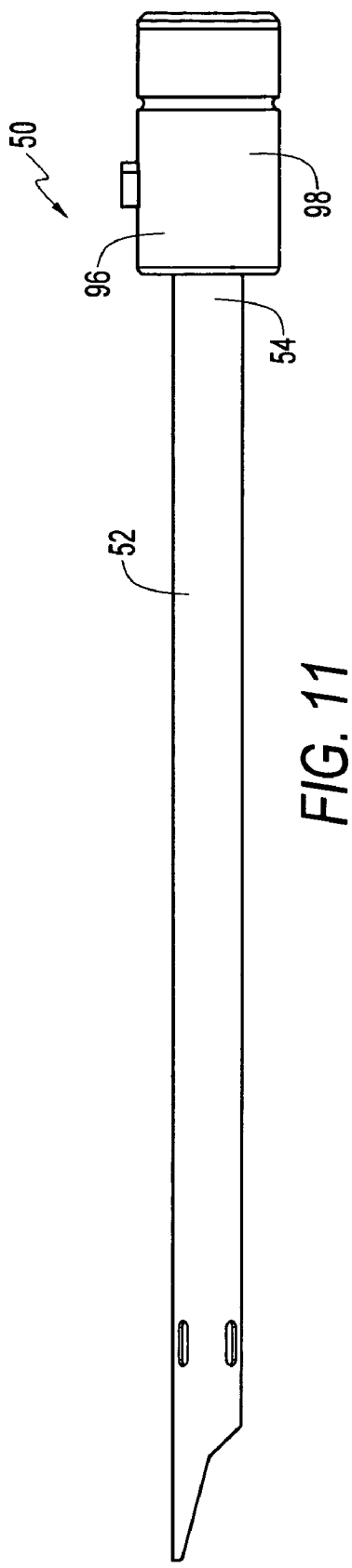
FIG. 10
FIG. 11

SECTION A-A  FIG. 12

D-D

SECTION A-A

B-B

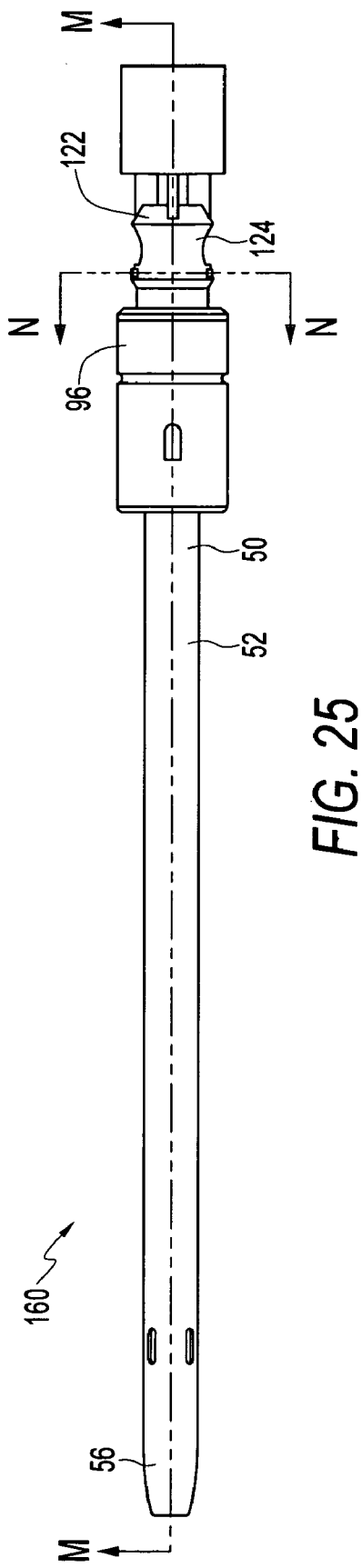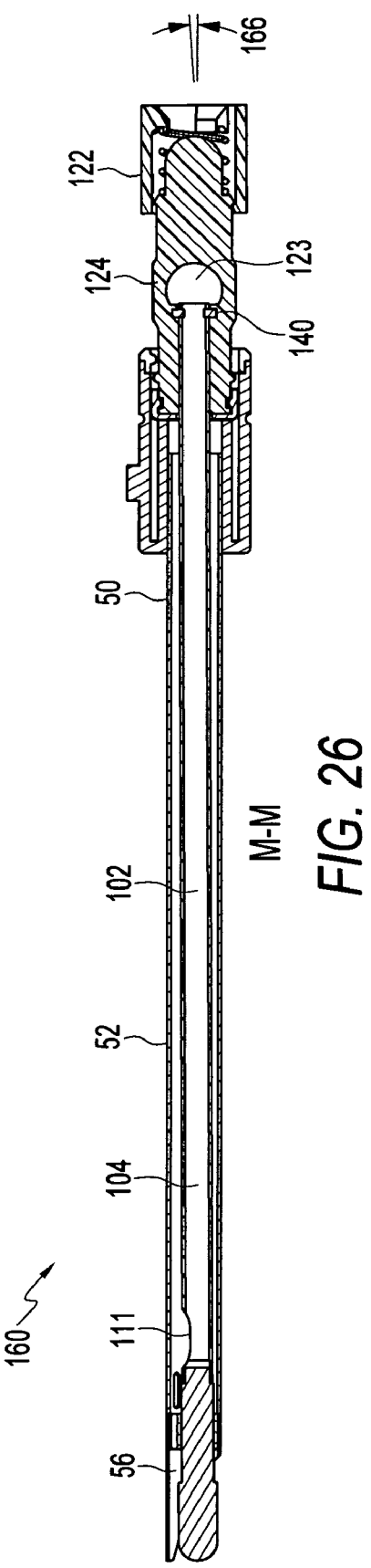
FIG. 25
FIG. 26

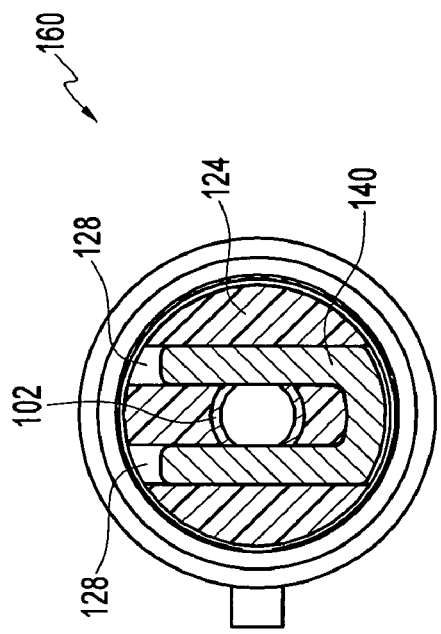
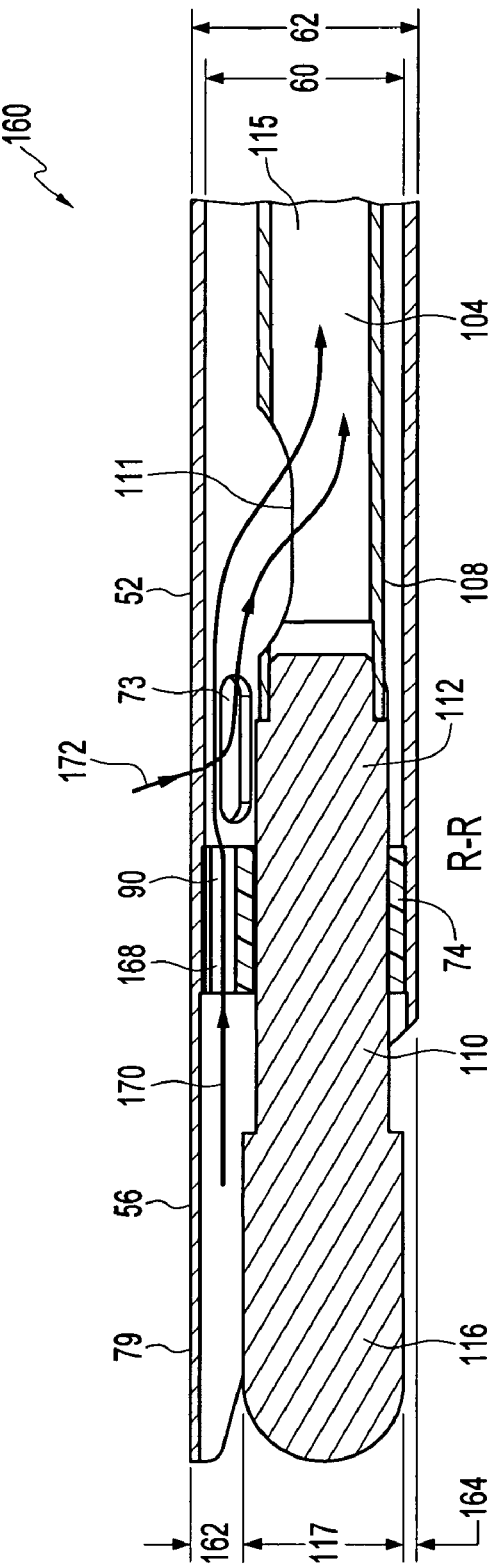

SECTION C-C

SECTION B-B

SECTION D-D

SECTION E-E

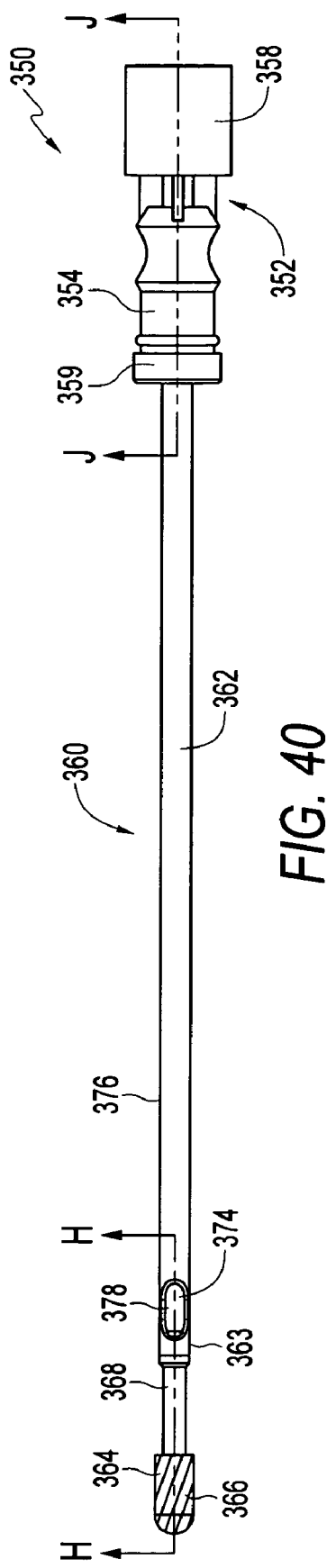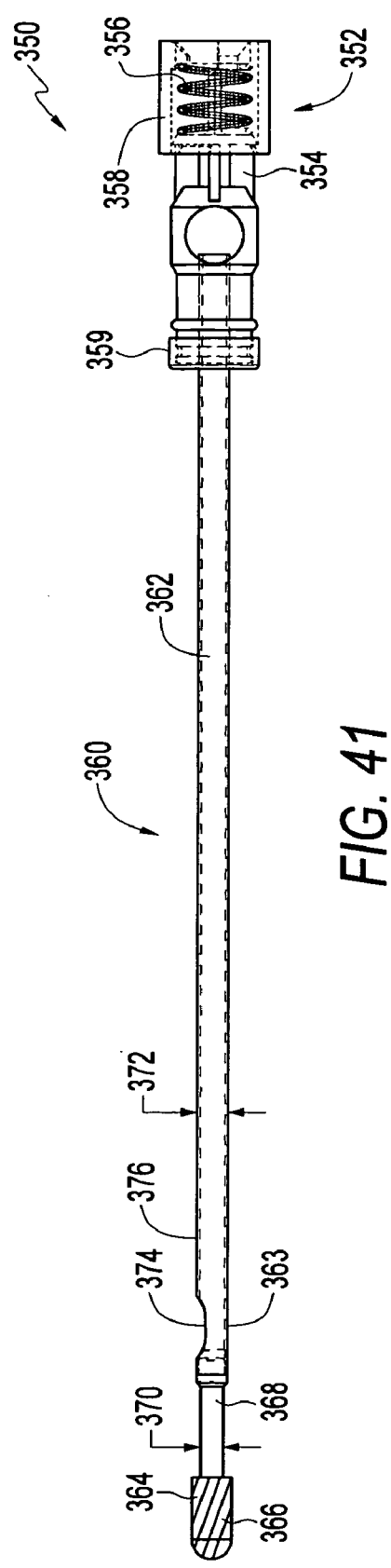

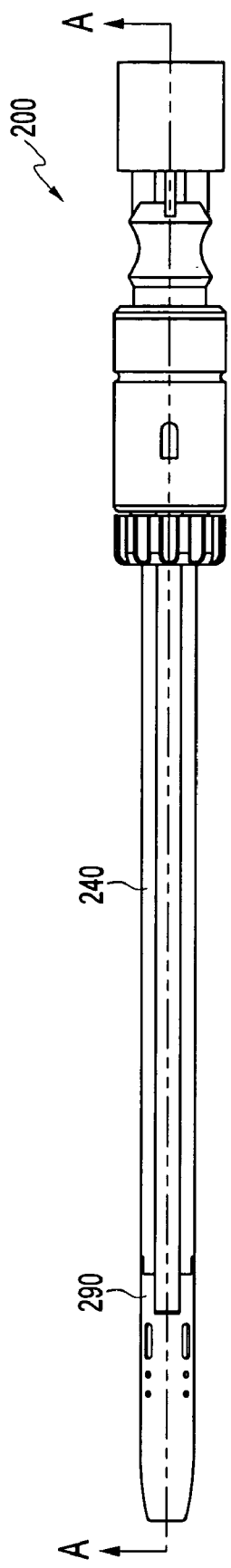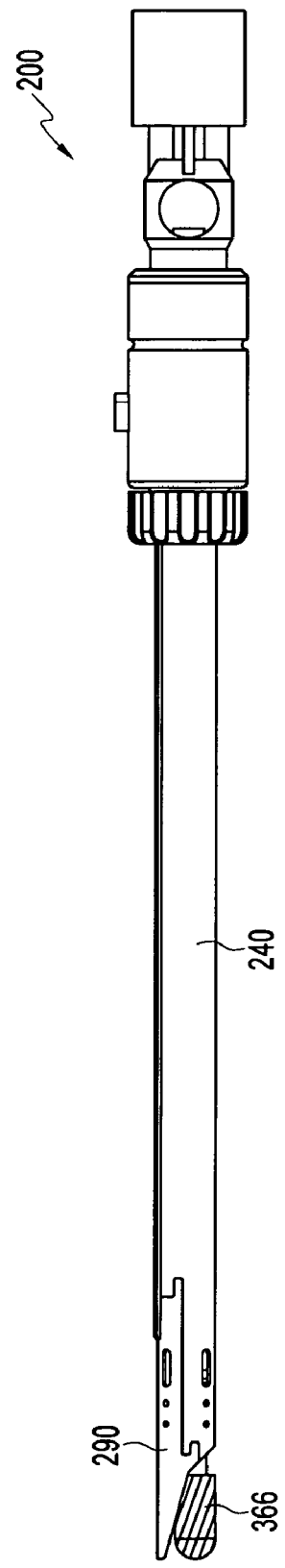

SECTION A-A

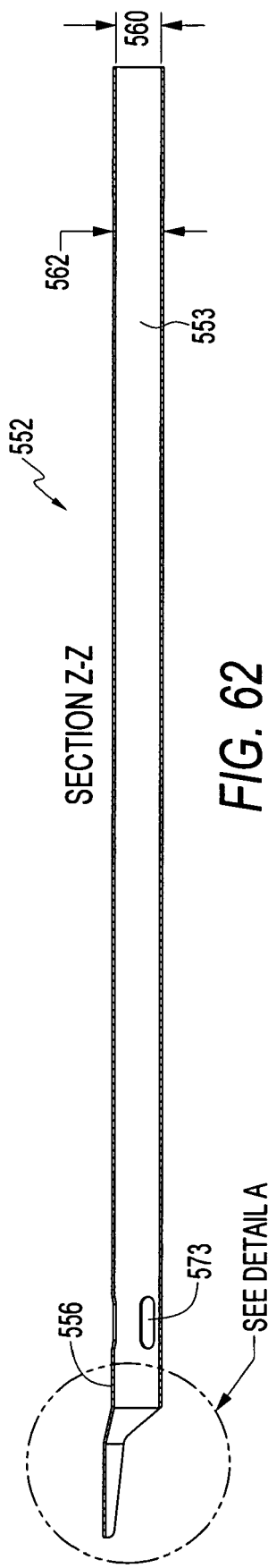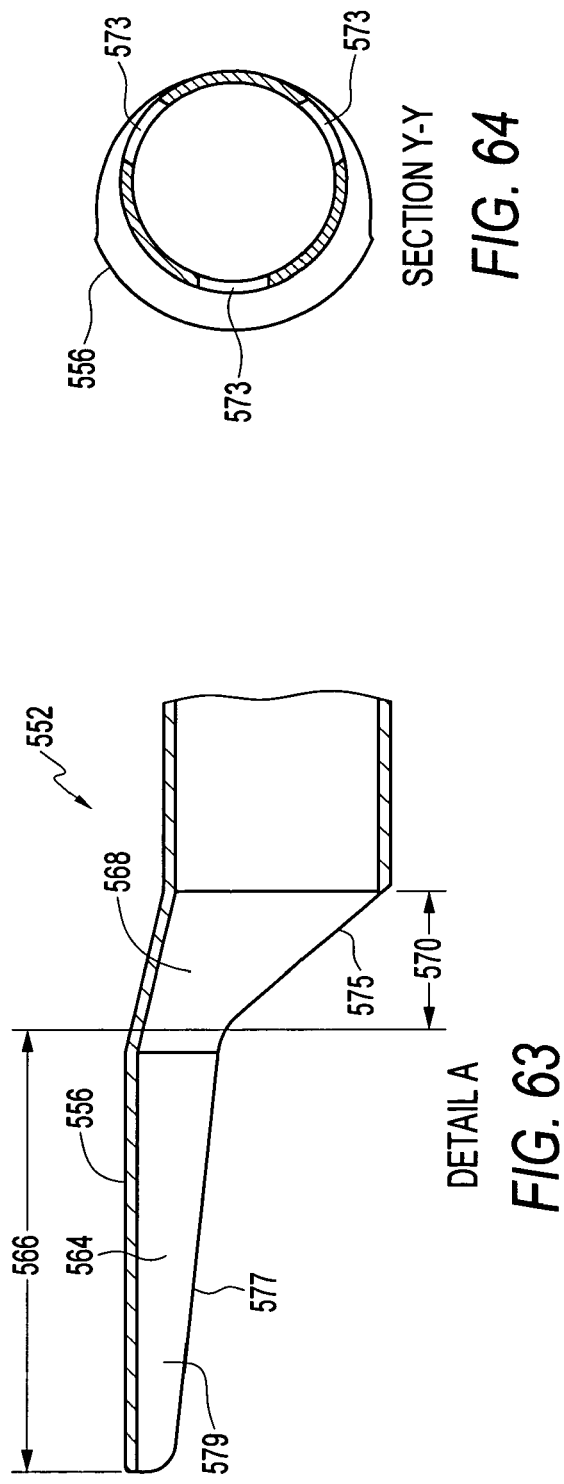

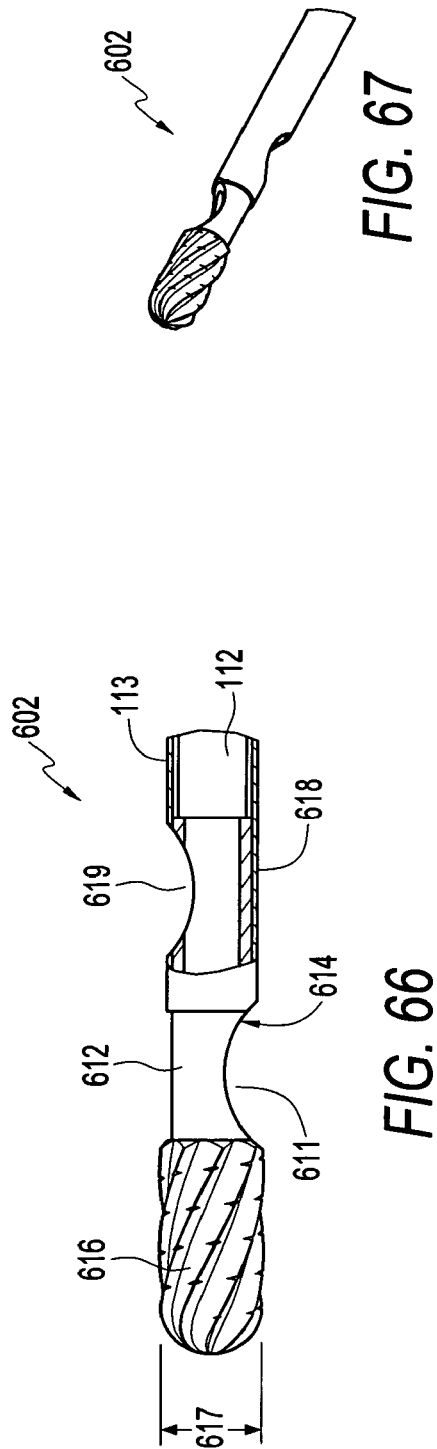
FIG. 65
FIG. 67
FIG. 66

ENDOSCOPIC ROTARY ABRADER

This application claims priority to U.S. Provisional Application No. 60/657,418 filed Mar. 2, 2005, the disclosure of which is incorporated herein in its entirety.

FIELD OF THE INVENTION

This invention relates to rotary abraders used in surgery and, more particularly, to an abrader which gives the surgeon an improved view of the surgical site during endoscopic surgery.

BACKGROUND OF THE INVENTION

Least invasive surgical techniques have gained significant popularity because of their ability to accomplish outcomes with reduced patient pain and accelerated return of the patient to normal activities. Arthroscopic surgery, in which the intraaticular space is filled with fluid, allows orthopedists to efficiently perform procedures using special purpose instruments designed specifically for arthroscopists. Among these special purpose tools are various manual graspers and biters, electro-surgical devices, and powered shaver blades and rotary abraders. Shaver blades having hollow bores are typically removably coupled to a shaver handpiece and are used for cutting, resecting, boring and abrading both soft and hard tissue at the surgical site. An arthroscopic abrader (also known as a burr) generally includes a rotatable inner tube having an abrading head at its distal end and a fixed outer tube for rotatably receiving the inner tube. Abraders are used for abrading or shaping both soft and hard tissue such as bone, cartilage, ligaments, etc. by use of the rotating abrading head. As the tissue is being abraded, debris and fluid are generally drawn or sucked through the rotatable inner tube.

Requirements for a rotary abrader for arthroscopy include a compact size so as to fit through small cannulae, a means for removal of debris, and a configuration which allows the surgeon to access structures within a joint, while retaining good visibility. One requirement for good visibility is the effective removal of debris as it is generated. Another is that the instrument be configured so that the view of the active portion of the abrader in contact with the tissue and the view of the tissue being abraded are not obscured by the instrument.

Rotary abraders for arthroscopy generally have a shield, also called a "hood," on one side of the distal end of the outer tube to prevent inadvertent injury to tissue in close proximity to the tissue being abraded. The distal end of this hood is angled with respect to the tube axis so as to expose only one side of the burr head. During use, the burr head (the abrading element at the distal end of the rotating inner member) is subjected to significant lateral forces. Although all rotary abraders have a bearing near the distal end of the instrument to support the inner member, lateral deflection of the burr head occurs. Contact between the burr head and the hood is undesirable since the burr will abrade metal from the hood and deposit metallic debris in the joint. Accordingly, it is necessary to leave adequate clearance between the hood and the burr head. The amount of clearance necessary is largely determined by the rigidity of the inner tube and the placement of the distal bearing between the inner and outer tubes. It is desirable to place the distal bearing as close as practical to the burr head to minimize deflection. It is also desirable to make the distal portion of the inner tube as rigid as practical. On currently available rotary abraders, the outer, stationery tube and inner, rotating tube are concentric. Because of this, the diameter of the distal portion of the outer, stationery tube in proximity to the burr head is significantly larger than the diameter of the burr head, so as to have adequate clearance. The required diameter of this portion of the outer tube is determined by the resistance of the burr head to deflection, which in turn is determined by the bearing placement and inner tube distal end construction. While this increased diameter prevents contact between the burr head and the hood, it also restricts the surgeon's access to some structures, and often obscures the surgeon's view of the site being abraded.

Removal of debris from the field is accomplished by aspirating the material from the joint via a lumen in the inner, rotating member which is connected through a means in the handpiece to an external vacuum source. The aspiration of material through the inner member is desirable as this allows easy transfer of the materials from the proximal end of the instrument to the aspiration passage of the handpiece. The manner in which material and fluid enter the lumen at the distal end of the instrument has a large effect on the volume of flow through the instrument and on the frequency with which the instrument clogs. Insufficient flow causes decreased visibility because of residual debris suspended in the intra-articular fluid. Clogging requires that the instrument be removed from the joint and "de-clogged". The degree of difficulty of clog removal is determined by the instrument design. Even if clog removal is easily accomplished, removing, de-clogging and reinserting the instrument is a nuisance and causes increased procedure times. Aspiration effectiveness, and therefore instrument design, have a large effect on burr efficiency.

Referring to FIGS. 1 through 5, prior art burr 10 has an inner assembly 12 rotatably positioned within an outer assembly 14. Inner assembly 12 has an proximal end 16 forming a hub assembly 18 for engaging the drive element of a powered handpiece, and an elongated tubular portion 20 having an abrading element 22 at its distal end 24. Bearing 26 is positioned near distal end 24 of tubular portion 20 slightly proximal to aspiration port 28 which provides a means of material flow to the lumen 21 of portion 20. Outer assembly 14 has a proximal end 30 forming a hub assembly 32 for removably mounting in a powered handpiece, and an elongated tubular portion 34 having a distal end 36 forming a beveled surface 38. As best seen in FIG. 4, bearing 26 centers distal end 24 of inner assembly 12 within distal end 36 of outer tubular portion 34 so as to maintain clearance 40 between abrading element 22 and shield (hood) 42 formed by distal end 36 and beveled surface 38. Clearance 40 is determined by the diameter 46 of burr head (abrading element) 22, and the inner diameter 47 and wall thickness 48 of outer tubular portion 34. Debris and liquid are aspirated from the region of abrading element 22 along path 44 to lumen 21 via aspiration port 28.

In U.S. Pat. No. 4,842,578, Johnson et al. teach an aspiration method in which material is drawn into the lumen of the inner tube via slots in the inner assembly distal to the bearing—the bearing is moved quite far proximal, thereby increasing the lateral deflection of the burr head during use. This, in turn, necessitates larger clearance between the burr head and the hood, and thus a large hood diameter, which obscures the surgeon's view and access. The relatively small slots in this design would make the instrument prone to clogging.

In U.S. Pat. No. 5,913,867, Dion teaches a rotary abrader with improved aspiration. As with the Johnson device, material is drawn into the lumen of the inner tube via an opening distal to the bearing between the inner and outer tubes. At least a portion of the opening is distal to the proximal end of the angled distal opening in the hood. This allows greater flow volumes and decreased clogging. However, the bearing is still proximal to the opening in the inner tube which allows for greater deflection of the abrading element during use. This necessitates that the hood diameter be significantly greater than the diameter of the burr head.

Vaca et al., in U.S. Pat. No. 6,053,923, teach a rotary abrader construction in which material is drawn into the lumen of the inner tube through axially aligned openings in the inner and outer tubes proximal to the distal end bearing. The inner and outer tubes may have a single opening or multiple openings. The openings admit liquid and tissue when angularly aligned and have a geometry designed to cooperatively cut tissue in the same manner as an arthroscopic shaver blade. The cutting action of the openings is intended to decrease clogging. The design is likely quite effective when the instrument is fully inserted into the joint, however, there will likely be instances in which the openings are obstructed because the burr is not fully inserted into a joint, or the joint is small. In these cases, it will be impossible to aspirate tissue through the instrument.

Grinberg, in U.S. Pat. No. 5,759,185, teaches a rotary abrader in which a lumen within the burr head extends distally such that openings in the troughs between the cutting flutes of the burr intersect the lumen. Debris is sucked into the openings while the burr is cutting tissue and removed from the site. A potential problem with this method is that the burr is rotating at high speed and the centrifugal force would tend to move material away from the openings. Also, it is likely that cavitation would tend to disrupt the flow of material into the openings, and proximally from the openings to the lumen in the inner tube.

Moutafis, in U.S. Patent Publication No. 2003/0055404, teaches a second stationary tube concentrically positioned about the standard stationery tube with a space between the tubes used to aspirate debris. It is likely that this passage would be prone to clogging unless it was made quite large, in which case the instrument diameter would be very large compared to that of the rotating abrading element. This, in turn, requires the use of large cannulae and generally obstructs the surgeon's view.

Moutafis, in U.S. Patent Publication No. 2003/0083681, teaches a distal bearing which does not have continual contact with the inner tube, but rather has contact regions separated by passages through which liquid and debris are aspirated. This allows the bearing to be placed quite close to the burr head as to minimize deflection, however, the decreased bearing surface will likely lead to higher forces between the bearing and the rotating member making galling and the generation of metallic debris more likely. Also, because of size constraints of the outer tube, the passages would be quite small and prone to clogging. Clearing clogs would be problematic since access to the passages is limited by the burr head, and the burr could not be readily disassembled for clearing as the burr head is larger in size than the bearing surfaces thereby preventing the inner portion from being withdrawn proximally.

U.S. Patent Publication No. 2004/0181251 by Hacker et al. describes a rotary abrader with multiple slots in the stationary outer tube proximal to the burr head and proximal to the distal bearing. A burr so constructed has excellent rigidity since the bearing is close axially to the burr head. It has good flow volume because of the number and size of the slots. If one or more slots become clogged by tissue the other slots still pass enough flow to allow the procedure to continue without having to remove and clear the instrument. A drawback of this construction, however, as in the case of the Vaca et al. device, is that the slots may be obstructed by tissue when the instrument is initially inserted into the joint, or when it is used on a small joint.

The rotary abraders previously herein considered may be generally divided into two categories: those which can be disassembled by withdrawing the inner tube proximally from the outer tube, and those which cannot be so dissembled. Most commercially available arthroscopy burrs fit into the first category. A burr which may be disassembled in this manner must of necessity have a bearing which is affixed to the inner member and is larger in diameter than the burr head, or alternatively have a portion of the rotating member proximal to the burr head with a larger diameter than the burr head to engage a bearing of the stationary outer member. The bearing is generally a thin polymeric or metallic layer applied to the inner which prevents galling between the inner and outer members. The inner member diameter is maximized to maximize the inner lumen size so as to increase flow volume and prevent clogging. Clogging, however, generally occurs at the distal end of the instrument, at the opening of the passage proximal to the burr head. The clogging most frequently occurs because soft tissue wraps around the inner member proximal to the burr. On burrs with a single opening, or with multiple openings in close proximity, a clog stops all aspiration of debris from the site and necessitates removal and clearing of the instrument for the surgical procedure to continue.

There is a need for an improved rotary abrader having rigidity, an aspiration means which effectively removes debris without clogging and which can be readily cleared of clogs without disassembly, and enhanced surgeon visibility.

It is accordingly an object of this invention to provide a rotary abrader with high resistance to deflection of the burr head.

It is also an object of this invention to provide a rotary abrader with improved visibility for the surgeon.

It is also an object of this invention to provide a rotary abrader able to produce high aspiration flow rates regardless of the insertion position of the instrument in the joint or the size of the joint.

It is further an object of this invention to provide a rotary abrader which has multiple aspiration openings so as to allow the instrument to be used with one or more openings partially for fully clogged.

SUMMARY OF THE INVENTION

The present invention achieves the foregoing objectives by providing, in one embodiment, a rotary abrader in which the inner member and outer member are not concentrically positioned. In this embodiment, the proximal end of the stationary outer member forms a hub for mounting to a handpiece, and the distal end has a generally laterally facing opening for exposing the burr head. A bearing is affixed to the tube inner lumen proximal to the opening. The inner surface of the bearing is not concentric with the outer tube, but rather is displaced laterally toward the laterally facing opening. Slightly proximal to the bearing are one or more elongated passages between the inner and outer surfaces of the tube. The bearing and outer tube together form axial passages which allow the flow of material from the distal side of the bearing to the proximal side. The passages are generally on the portion of the bearing that is away from the generally lateral facing opening. The rotating inner member has a proximal end forming a hub which engages a driving mechanism within a handpiece and an elongated portion, the distal end of which forms an abrading element. Proximal to the abrading element is a portion having a diameter less than that of the abrading member. Proximal to this portion is a tubular portion which extends proximally to the proximal end of the inner member. This tubular portion has an opening forming an aspiration port near its distal end which allows the flow of materials into the lumen of the tubular portion.

During use, liquid and debris are aspirated from the joint along two paths which join at the aspiration port in the inner tube. The first path, taken by debris and liquid in close proximity to the abrading element, is through the axial passages formed in the bearing to the aspiration port. The second path, taken by debris and liquid in the region adjacent to the instrument's distal end, is through the elongated passages between the outer and inner surfaces of the outer tube proximal to the bearing, going to the aspiration port in the inner tube. Material then flows via the lumen in the inner tube to the handpiece from which it is removed by an external vacuum source. This two-path aspiration is advantageous in that debris is removed through multiple external openings. If one or more openings get partially or completely clogged, aspiration continues through the remaining clear openings. Some clogging can be tolerated without removal of the instrument from the joint. Aspiration via the elongated slots in the outer tube increases the flow volume when the instrument has been inserted to sufficiently remove obstruction of the slots by tissue. Until these slots are unobstructed, debris is removed through the axial end of the outer tube via passages formed by the slots in the bearing. Clogs are easily removed. Clogs at the elongated slots are easily accessible while clogs in the passages formed by grooves in the bearing are accessible through the instrument's distal end. Access to these passages is not prevented by the burr head. Because the aspiration port in the inner assembly distal region is much larger than the elongated openings in the outer tube or the passages in the bearing, clogging of the aspiration port does not occur.

In one embodiment, the inner assembly is formed of two subassemblies. The first, distal subassembly has a burr head (abrading element) at its distal end, a cylindrical portion adjacent to the burr head, and an elongated tubular portion with a fastening means at its proximal end. The second, proximal subassembly had a hub with a driving means and a fastening means for affixing the proximal subassembly to the distal assembly. The diameter of the cylindrical portion proximally adjacent to the burr head has a smaller diameter than the burr head. The tubular, proximal portion has a smaller diameter than the cylindrical portion. The distal subassembly of the inner assembly is inserted into the distal end of the outer assembly. The proximal subassembly is affixed to the proximal end of the tubular portion by the fastening means to produce the complete instrument. The cylindrical portion of the inner assembly is rotatably positioned within the distal bearing.

The resistance of the burr head to lateral deflection is enhanced by the placement of the bearing in close proximity to the burr head. The burr head is shifted away from the hood by the offset in the bearing. This combination of enhanced rigidity and eccentricity of the inner assembly and outer tube allows the diameter of the outer tube to be decreased, or the diameter of the abrading element to be increased, thereby minimizing obstruction of the surgeon's view and improving access to structures within a joint.

In another embodiment, the distal and proximal portions of the inner assembly are permanently affixed. The inner assembly has a burr head at its distal end, a cylindrical portion proximally adjacent to the burr head, and an elongated tubular portion with a hub with a drive means at its proximal end. The diameter of the cylindrical portion is less than the diameter of the burr head and, in contrast with the previous embodiment, smaller than the diameter of the tubular portion. The outer assembly, which has a tubular portion and a proximal portion forming a hub, is composed of two subassemblies. The distal bearing is split axially to form two portions with a bearing portion attached to each of the outer subassemblies. The distal portion of the tubular portion is divided into an upper portion and a lower portion. The lower portion, with a fastening means for removal attaching it to the upper portion, forms the first subassembly. A first bearing portion is mounted to the upper (lumen) side of the subassembly near its distal end. The proximal end of the first subassembly forms a hub for removably mounting the abrader to a handpiece. The upper portion, with a fastening means for removal attaching it to the lower portion forms the second subassembly, a second bearing portion being mounted to the lower (lumen) side of the portion near its distal end. The distal end of this second subassembly forms a hood.

The abrader is assembled in two steps. The inner assembly is inserted into the first outer subassembly so that the cylindrical portion of the inner assembly is rotatably positioned in the first portion of the distal bearing. The second outer subassembly is then removably mounted to the first subassembly so as to form a complete outer assembly with the inner assembly rotatably positioned within it. The cylindrical portion of the inner assembly is positioned within the bearing formed by the first and second bearing portions.

The unique construction of this second embodiment provides advantages for certain applications. In the first embodiment, the diameter of the cylindrical portion of the inner assembly is greater than the diameter of the tubular portion, so as to allow the inner assembly to be inserted proximally into the bearing of the outer assembly. The tubular portion must be of sufficient diameter to transmit required torque to the abrading element, and have a lumen of sufficient size for effective aspiration. The minimum diameter for the tube determines the minimum diameter of the cylindrical element, which, in turn, determines the bearing configuration and the distance that the burr head can be shifted laterally away from the hood.

In the second embodiment, the cylindrical portion of the inner assembly can be smaller than the tubular portion since the inner assembly is not inserted into the bearing axially but rather is positioned between two halves of a split bearing. This allows the displacement between the center of the outer tube and the center of the inner assembly to be increased, allowing further increase in the clearance between the burr head and the hood for a given tube size. This, in turn, gives improved visibility for the surgeon and enhanced access to structures within a joint. Another advantage of the second embodiment is the ease of disassembly and reassembly for cleaning. This is essential for a reusable instrument.

In a third embodiment of the present invention, the inner and outer assemblies are concentric, rather than offset, but the inner assembly is provided with an enlarged burr head at the distal end. To maintain the required clearance between the enlarged burr head and the hood, the hood is positioned at an angle and enlarged.

In the various embodiments of the present invention, the enlarged burr is preferably configured so that its cutting edge is aligned with the outer surface of the outer tube to provide a "flush cut."

BRIEF DESCRIPTION OF THE DRAWINGS

The above described features of the invention will be more clearly understood from the following detailed description, which is provided with reference to the accompanying drawings.

FIG. 2 is a plan view of the prior art rotary abrader of FIG. 1 assembled.

FIG. 3 is a side elevational view of the objects of FIG. 2.

FIG. 5 is a plan view of the outer tube of a rotary abrader in accordance with a first embodiment of the invention.

FIG. 6 is a side elevational view of the objects of FIG. 5.

FIG. 7 is an expanded side sectional view of the distal portion of the objects at location A-A of FIG. 5.

FIG. 8 is a side elevational view of the distal bearing of a rotary abrader constructed in accordance with a first embodiment of the invention.

FIG. 9 is an axial view of the objects of FIG. 8.

FIG. 10 is a plan view of the outer assembly of a rotary abrader constructed in accordance with a first embodiment of the invention.

FIG. 11 is a side elevational view of the objects of FIG. 10.

FIG. 25 is a plan view of the objects of FIG. 24 when assembled.

FIG. 26 is a side elevational sectional view of the objects at location M-M of FIG. 25.

FIG. 27 is an expanded axial sectional view of the objects at location N-N of FIG. 25 showing the position of the retainer in the inner hub.

FIG. 28 is an expanded side sectional view of the distal end of the objects of FIG. 25, showing the aspiration paths.

FIG. 40 is a plan view of the inner assembly of the embodiment of FIG. 29.

FIG. 41 is a side elevational view of the objects of FIG. 40.

FIG. 52 is a plan view of the assembled a rotary abrader constructed in accordance with a second embodiment of the invention.

FIG. 53 is a side elevational view of the objects at location A-A of FIG. 52.

FIG. 62 is a side elevational sectional view of the objects at location Z-Z of FIG. 60.

FIG. 63 is an expanded side elevational sectional view of the objects at location A of FIG. 62.

FIG. 64 is an expanded axial sectional view of the objects at location Y-Y of FIG. 61.

FIG. 65 is a plan view of the inner tube of a rotary abrader in accordance with a third embodiment of the invention.

FIG. 66 is an expanded plan view of the distal end of the inner tube of a rotary abrader in accordance with a third embodiment of the invention.

FIG. 67 is a perspective view of the distal end of the inner tube of a rotary abrader in accordance with a third embodiment of the invention.

DESCRIPTION OF THE PREFERRED EMBODIMENTS

Figure 1:
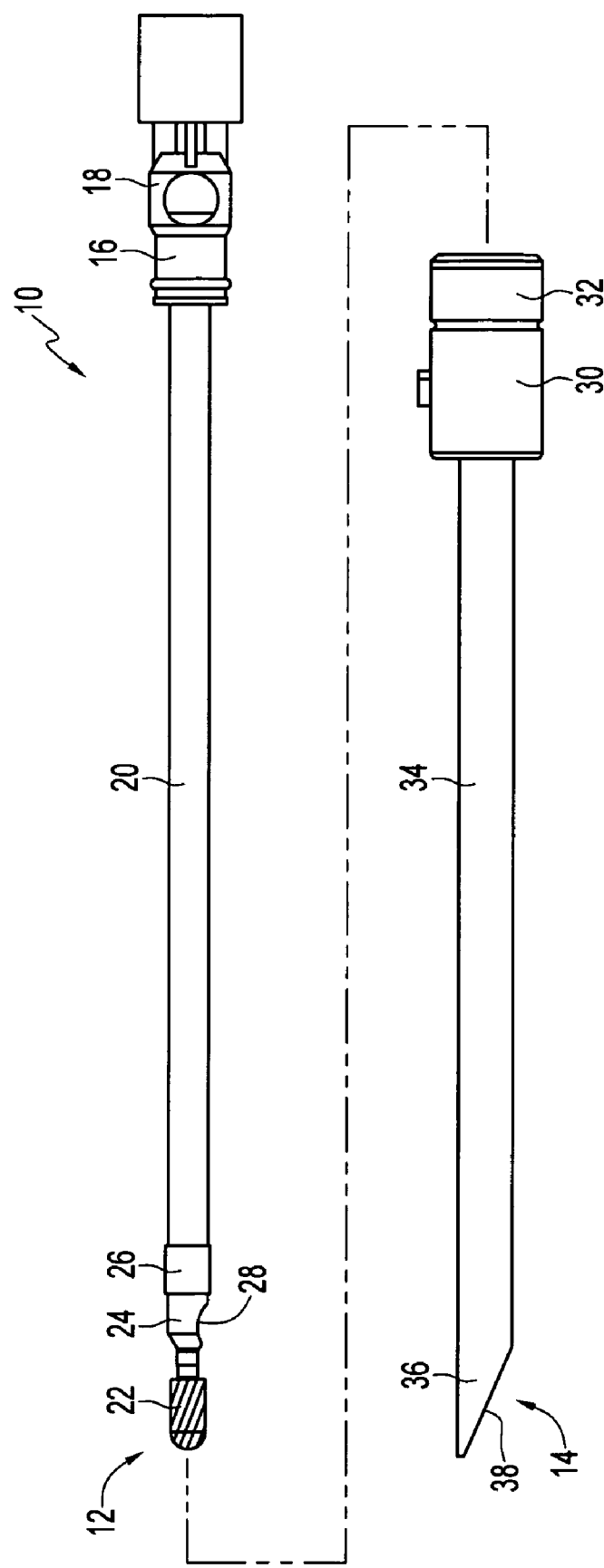
FIG. 1 is a side elevational view of a prior art abrader with the inner assembly disassembled from the outer assembly.
Figure 4:
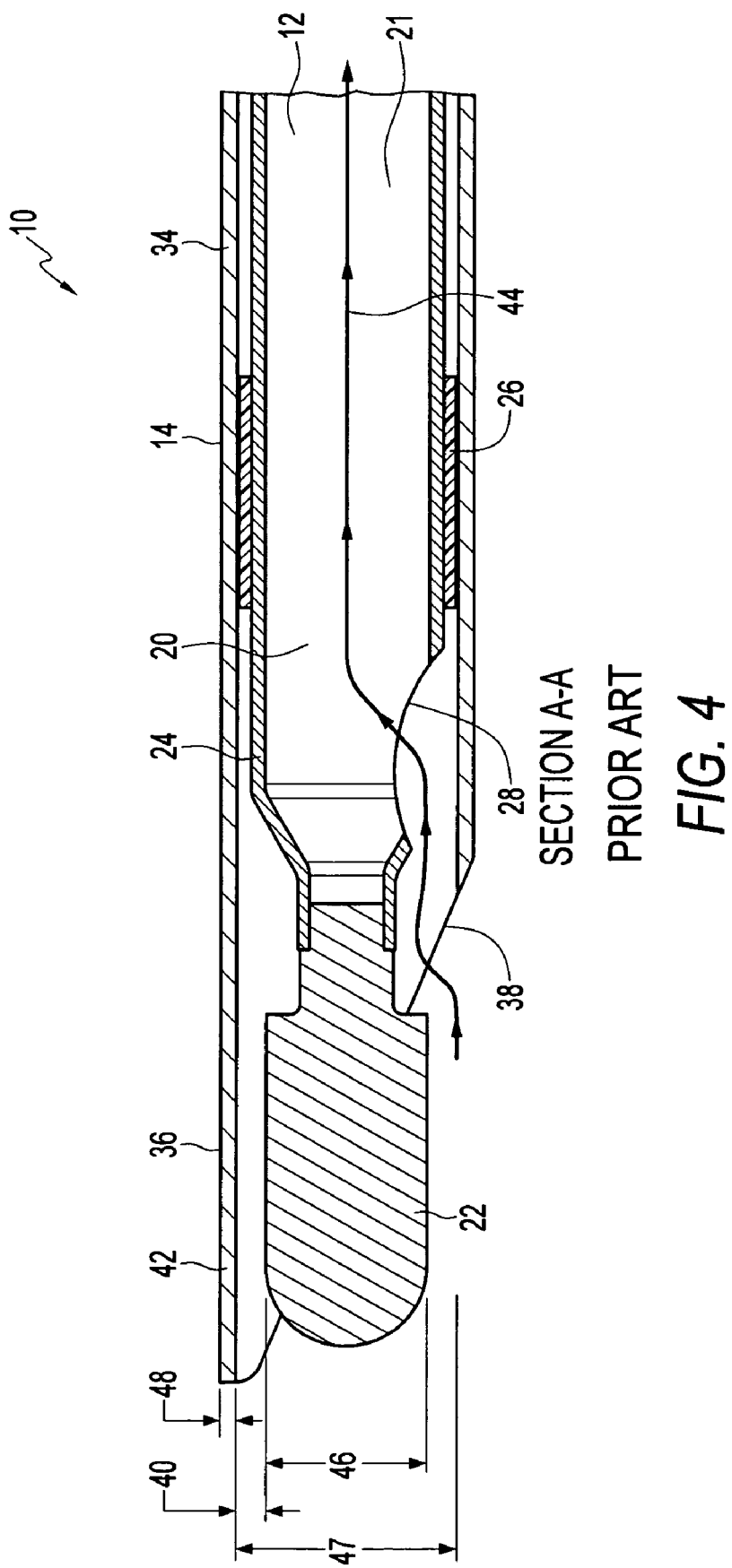
FIG. 4 is an expanded side elevational sectional view of the distal end of the objects at location A-A of FIG. 2.

In a first embodiment of the present invention, an inner assembly is rotatably positioned within an outer assembly. The proximal ends of the assemblies form hubs as in the prior art device of FIGS. 1 through 4. The elongated tubular portions of the inner and outer assemblies are not concentric, but rather have the inner tubular portion laterally positioned away from the hood so that required clearance can be maintained between the burr head and the hood while increasing the diameter of the burr head, or decreasing the diameter of the outer tube.

Referring now to FIGS. 5 through 7, showing the outer tubular portion (outer tube) 52 of the outer assembly 50 (FIG. 10) of a rotary abrader formed in accordance with the first embodiment of the invention, outer tube 52 has a proximal end 54 and a distal end 56. Tube 52 has a lumen 53 of diameter 60 and an outer diameter 62. Distal end 56 has a first portion 64 with an inner diameter 66 formed therein, and a second portion 68 of length 70 with a diameter 72 formed therein. Diameter 72 is slightly larger than diameter 60. Diameter 66 is slightly larger than diameter 72. Elongated slots 73 extended from the lumen 53 to tube outer surface 55. Beveled surfaces 75 and 77 together with outer surface 55 define a hood (or guard) 79.

FIGS. 8 and 9 show the distal bearing 74 of a rotary abrader formed in accordance with the principles of this invention. Bearing 74 has a cylindrical outer surface 76 of radius 78 and an inner bore 80 of diameter 82, the center of outer surface 76 and bore 80 being displaced a distance 84. Radius 78 is slightly larger than half of diameter 66 of first portion 64 of outer tube 52 (FIG. 7). Grooves 90 extended axially from distal surface 92 to proximal surface 94. Bearing 74 is made from a suitable polymeric or metallic material. Thickness 93 is approximately equal to length 70 of second portion 68 of outer tube 52 (FIG. 8).

Figure 12:
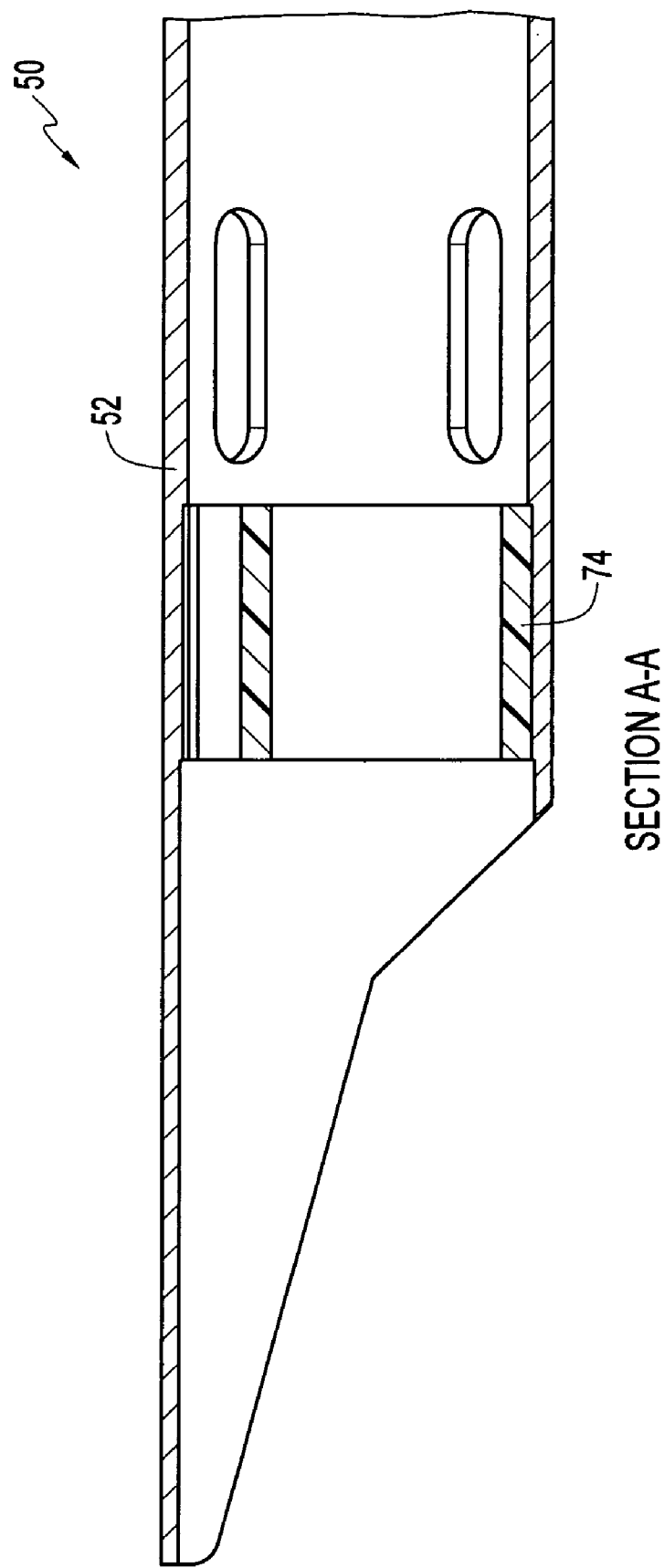
FIG. 12 is an expanded side sectional view of the distal portion of the objects at location A-A of FIG. 10.
Figure 13:
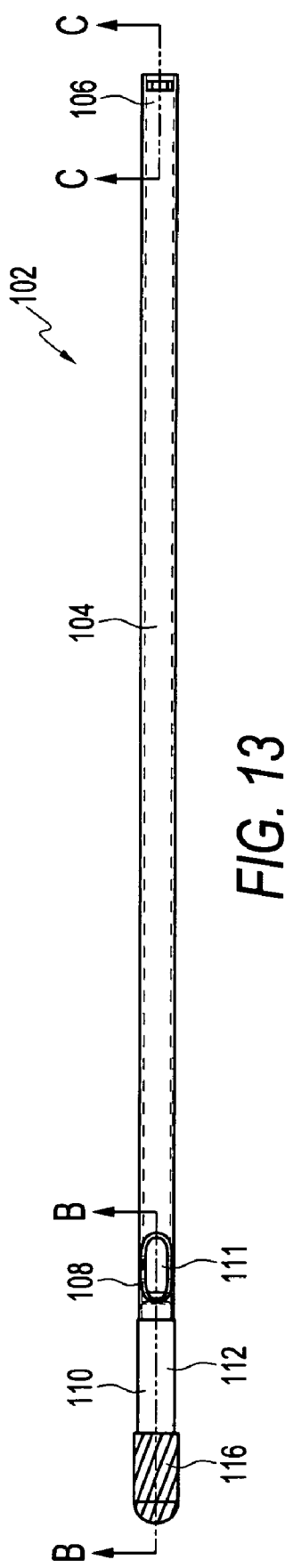
FIG. 13 is a plan view of the distal subassembly of the inner assembly of a rotary abrader constructed in accordance with a first embodiment of the invention.
Figure 14:
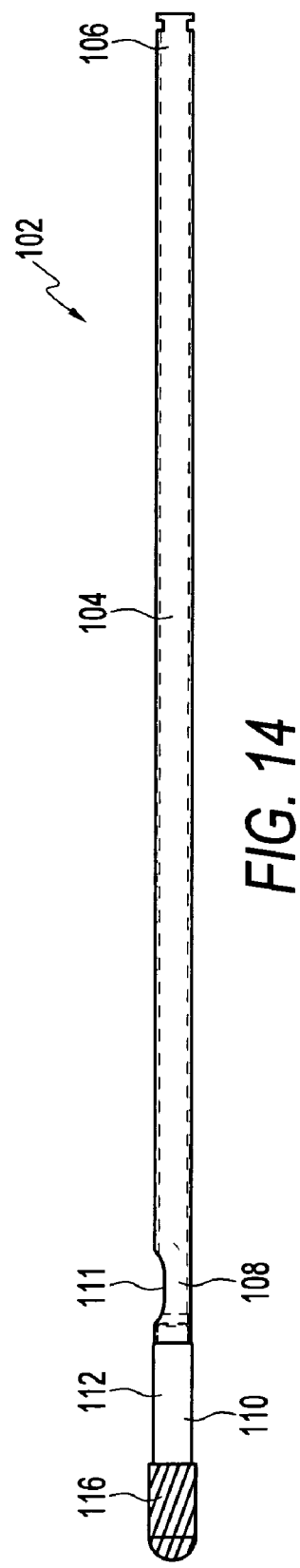
FIG. 14 is a side elevational view of the objects of FIG. 13.
Figure 15:
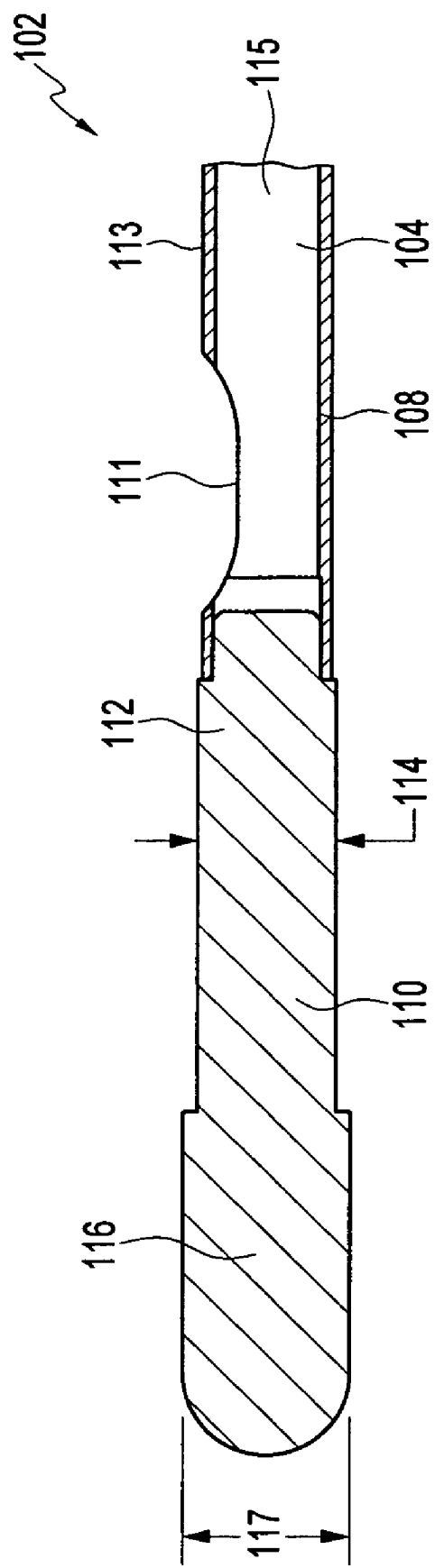
FIG. 15 is an expanded side elevational sectional view of the distal portion of the objects at location B-B of FIG. 13.

Referring now to FIGS. 10 through 12, outer assembly 50 has a proximal end 96 with a hub 98 affixed to proximal end 54 of tube 52. Bearing 74 is pressed into second portion 68 (FIG. 7) of outer tube 52 (FIGS. 5 and 6).

Figure 16:
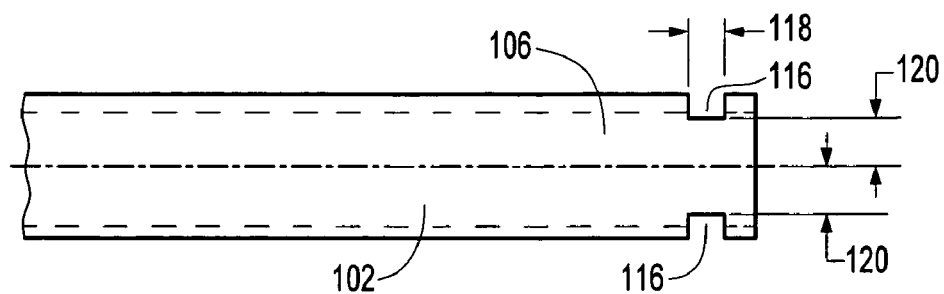
FIG. 16 is an expanded side elevational view of the proximal portion of the objects at location C-C of FIG. 13.
Figure 17:
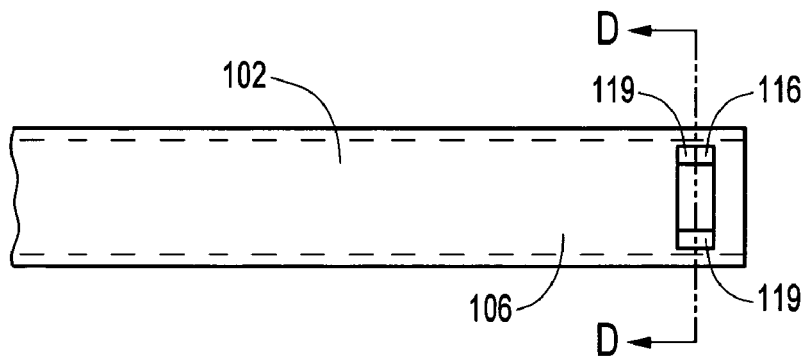
FIG. 17 is an expanded plan view of the objects of FIG. 16.
Figure 18:
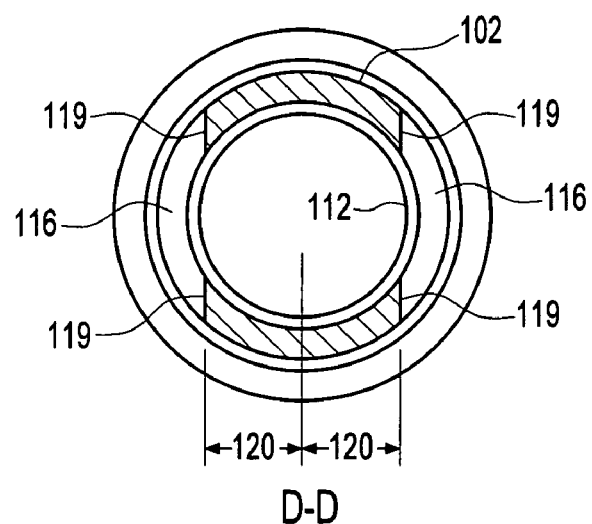
FIG. 18 is an expanded axial sectional view of the objects of FIG. 16 at location D-D of FIG. 17.

Referring now to FIGS. 13 through 17, inner tube assembly 102 of inner assembly 100 of a rotary abrader constructed in accordance with the principles of the invention has an elongated tubular portion 104 with a proximal end 106 and a distal end 108. Distal end 108 has affixed thereto portion 110 having a proximal portion 112 of diameter 114, and a distal portion 116 forming an abrading element (or burr head) of diameter 117. Diameter 114 is slightly less than diameter 82 of bore 80 of bearing 74 (FIG. 9). Near distal end 108 of tubular portion 104 aspiration port 111 extends from lumen 115 to outer surface 113. As best seen in FIGS. 16 through 18, proximal end 106 of tube 102 has formed therein slots 116 of width 118 so as to form flats 119 displaced a distance 120 from the center of tube 102.

Figure 19:
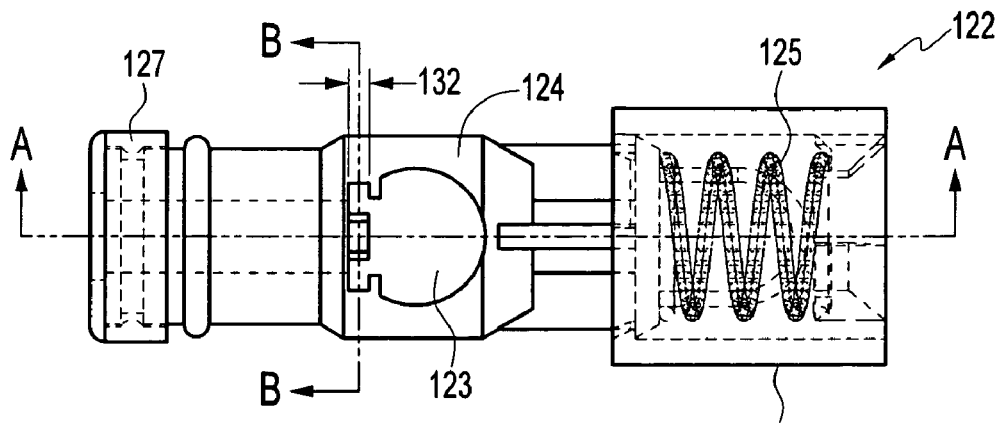
FIG. 19 is a plan view of the proximal hub subassembly of the inner assembly of a rotary abrader constructed in accordance with a first embodiment of the invention.
Figure 20:
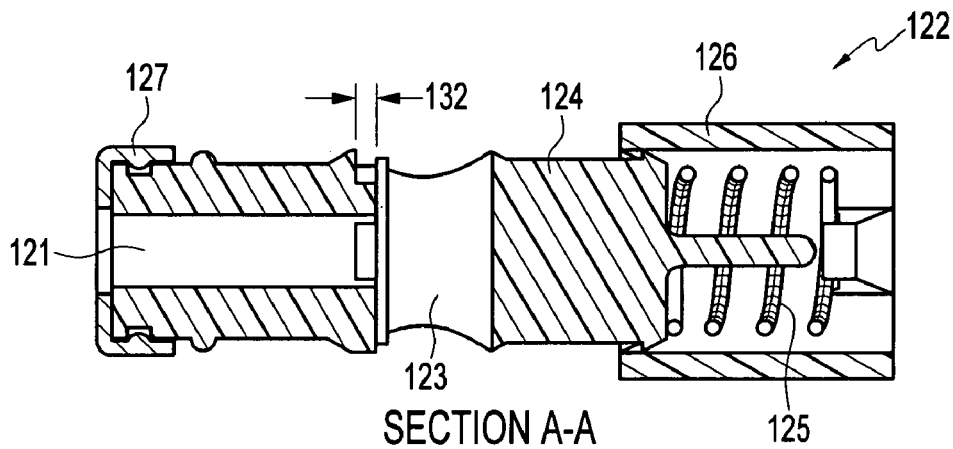
FIG. 20 is a side elevational view of the objects at location A-A of FIG. 19.
Figure 21:
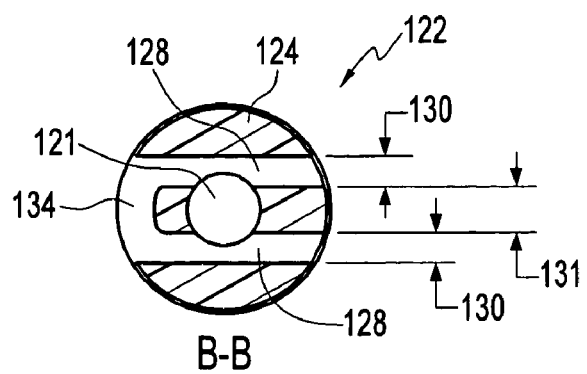
FIG. 21 is an axial sectional view of the retaining slot portion of the objects at location B-B of FIG. 19.

Referring now to FIGS. 19 through 21, showing inner hub assembly 122 of inner assembly 100, assembly 122 includes inner drive hub 124, spring 125, spring retainer 126 and thrust washer 127. Hub 124 has formed therein slots 128 of width 130 and depth 132 joined by portion 134 also of depth 132. Depth 132 is approximately equal to width 118 of slots 116 of tube 102 (FIG. 16). Slots 128 are separated by a distance 131 which is slightly greater than twice distance 120 that flats 119 are displaced from the center of tube 102 (FIGS. 17 and 18). Lateral aspiration passage 123 intersects bore 121.

Figure 22:
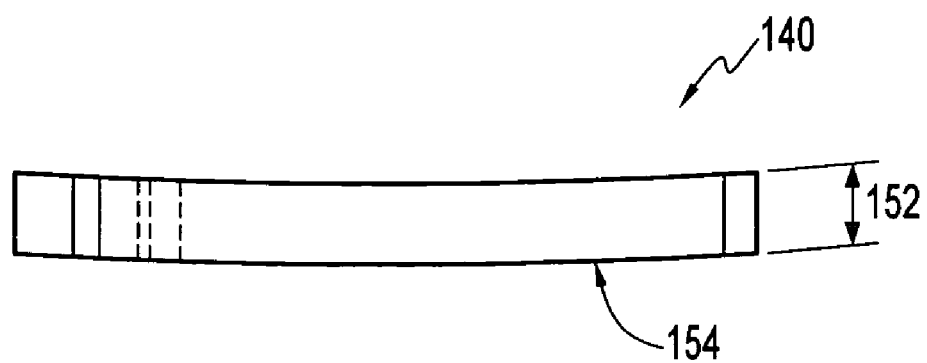
FIG. 22 is a side elevational view of the retainer for affixing the inner hub to the inner tube of a rotary abrader constructed in accordance with a first embodiment of the invention.
Figure 23:
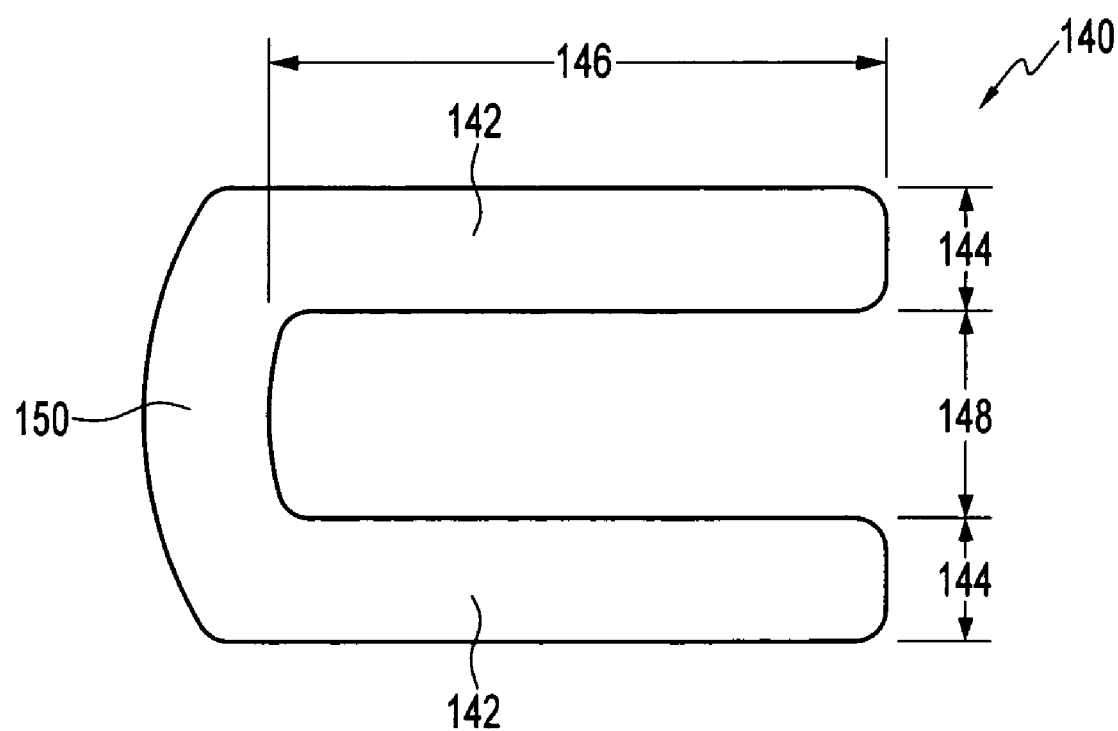
FIG. 23 is a plan view of the object of FIG. 22.

Retainer 140, shown in FIGS. 22 and 23, is part of inner assembly 100. The retainer is generally "U" shaped, with two leg portions 142 of width 144 and length 146 spaced a distance 148 apart and joined by a portion 150. Retainer 140 has a thickness 152, and is formed to a radius 154. Thickness 152 is slightly smaller than depth 132 of slots 128 in inner hub 124 (FIGS. 19 and 20) and width 118 of slots 116 of tube 102 (FIG. 16). Width 144 is approximately equal to width 130 of slots 128 of inner hub 124 (FIG. 21). Distance 148 is approximately equal to distance 131 between slots 128 of inner hub 124 (FIG. 21) and slightly greater than twice distance 120 that flats 119 are displaced from the center of tube 102 (FIGS. 16 and 18). Retainer 140 is made from a suitable metallic or polymeric material.

Figure 24:
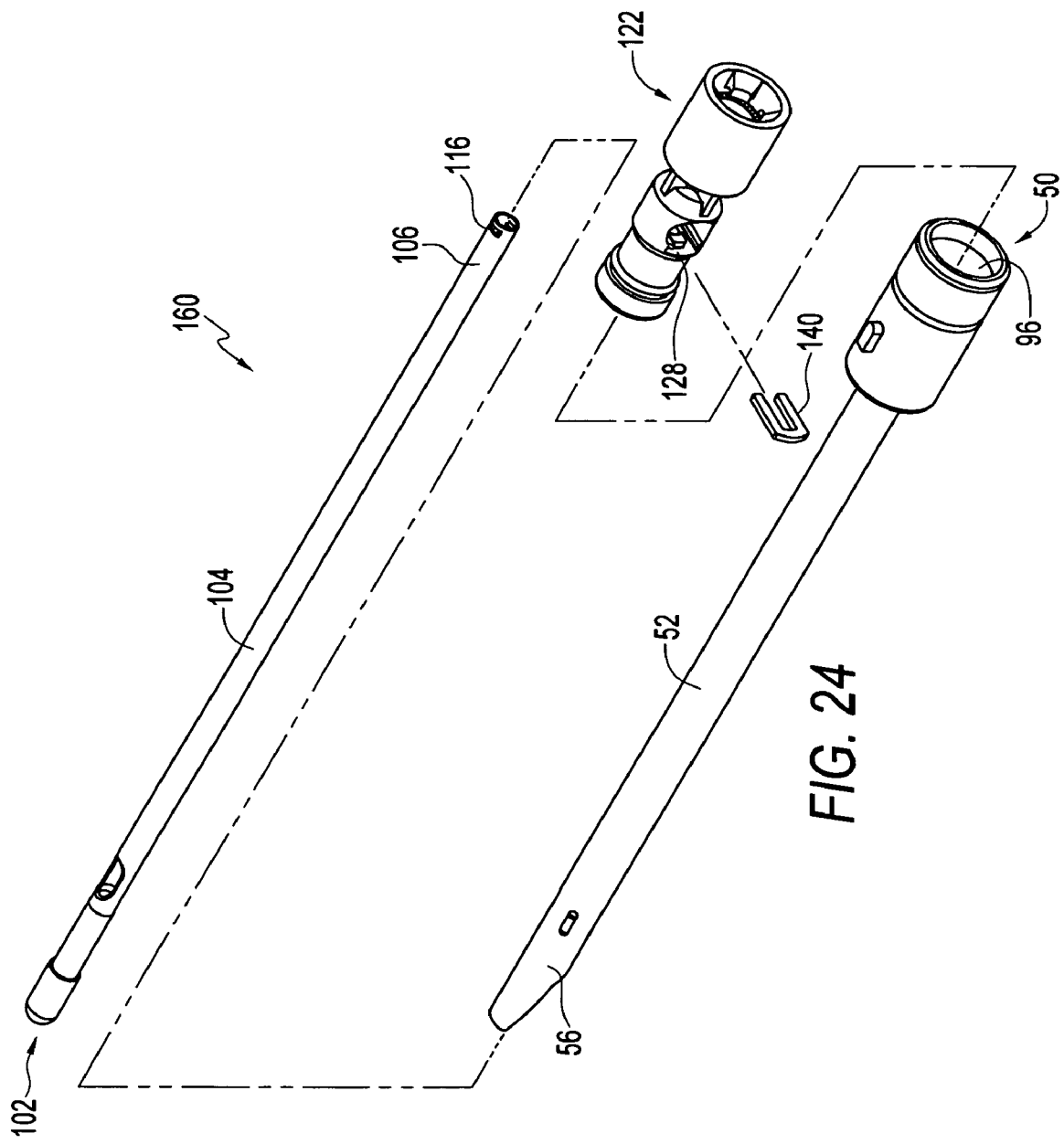
FIG. 24 is an exploded view of a rotary abrader constructed in accordance with a first embodiment of the invention showing the method of assembly.

Referring now to FIG. 24, rotary abrader 160, constructed in accordance with the principles of this invention, is assembled in the following manner. Tubular portion 104 of inner tube assembly 102 is inserted into distal end 56 of outer tube 52 of outer assembly 50. Hub assembly 122 of inner assembly 100 is inserted into proximal end 96 of outer assembly 50 such that proximal end 106 of tubular portion 104 of inner tube assembly 102 is positioned within inner hub 124 and slots 116 of tube 104 align axially and angularly with slots 128 of inner hub 124. Referring now also to FIGS. 25 through 27, retainer 140 is inserted into slots 128 thereby engaging slots 116 (FIGS. 16 through 18) so as to establish and maintain the axial and angular positioning of tubular portion 102 and hub 124. Deflection of the curved retainer 140 (radius 154, FIG. 18) by the straight slots 128 of inner hub 124 causes high frictional forces between retainer 140 and hub 124 thereby retaining retainer 140 within hub 124. While the axis of the inner assembly 102 is coplanar with the axis of the outer assembly 50 when viewed in a plan view, as best seen in the side elevational section view of FIG. 26, inner assembly 102 is offset angularly by angle 166 from outer assembly 50. Angle 166 is determined by distance 84 between the center of the radial outer surface 76 and the center of bore 80 of bearing 74 (FIGS. 9 and 10), and the distance between bearing 174 and the proximal end of inner assembly 102 which is centered in the handpiece.

As best seen in FIG. 28 showing an expanded section view of the distal portion of abrader 160, bearing 74 is positioned at proximal portion 112 of portion 110 (FIG. 15) distal to aspiration port 111 of inner tube 104, near the abrading element 116. This position minimizes deflection of element 116 (the burr head) when it is subjected to lateral forces. Clearance 162 is equal to the difference between inner diameter 66 of outer tube 52 (FIG. 7) and diameter 117 of abrading element 116, plus distance 84 between the center of the radial outer surface 76 and the center of bore 80 of bearing 74 (FIGS. 9 and 10). Distance 164 is equal to the difference between outer diameter 62 of outer tube 52 and outer diameter 117 of element 116, less distance 84 between the center of the radial outer surface 76 and the center of bore 80 of bearing 74 (FIGS. 9 and 10). Decreasing distance 164 increases the surgeon's view of the burr during use, and increases the ability of the burr to access structures during use.

Referring further to FIG. 28, during use, debris is aspirated from the site along two paths which join in lumen 115 of inner tube 104, from which the debris is removed via aspiration passage 123 in inner hub 124 (see FIG. 26) by suction supplied by the handpiece. Debris in close proximity to burr head 116 follows path 170 through passage 168 formed by groves 90 in bearing 74 (FIGS. 9 and 10) to aspiration port 111 in inner tube 104. Debris in the liquid in proximity to distal end 56 of outer tube 52 is aspirated along path 172 via slots 73 to aspiration port 111 in inner tube 104.

Because the abrading element of abrader 160 is not concentrically positioned within the outer tube, but is displaced away from the hood, the diameter of the abrading element can be increased and still maintain the minimum clearance required between the element and the hood. This allows the use of a larger abrading element for a given outer tube diameter than would be possible if the inner and outer members were concentric. This larger diameter burr allows more rapid removal of bone than the smaller diameter burr of a conventional burr having the same outer tube diameter. The larger diameter burr can also advantageously be configured so that its cutting edge is aligned with the outer surface of the outer tube to provide a "flush cut."

The material from which retainer 140 is made is determined by the intended life of the instrument, since reusable instruments must be disassembled for cleaning. In embodiments designed for disposal after a single use, retainer 140 may be made from a material which will degrade if the instrument is sterilized in an autoclave. In embodiments designed for reuse, retainer 140 is made from a durable material so that retainer 140 can be removed, the instrument cleaned and sterilized, and the instrument re-assembled using retainer 140. In some embodiments retainer 140 has features which facilitate removal and reinsertion of the retainer for instrument disassembly, cleaning and reassembly.

Changes may be made to the form of retainer 140 and inner hub 124 without violating the principles of this invention. For instance, inner tubular portion 104 may have the diameter of the proximal portion which assembles into hub 124 reduced so that retainer 140 must only prevent tubular portion 104 from moving distally out of the hub, the proximal movement of 104 being prevented by the shoulder created by the reduced diameter. Retainer 140 may also take other forms. For instance, tubular portion 104 may be retained in hub 124 by various threaded, locking, or interfering means without violating the principles of this invention.

The construction of abrader 160 requires that the diameter 114 of portion 112 of the inner member 102 at the distal bearing 74 be greater than the outer diameter of the inner portion tubular member 104 so that the inner assembly 102 can be inserted into the outer assembly 50 from the distal end. The minimum diameter of the inner tubular member is determined by the level of torque which must be supplied to the abrading element and by the lumen size required for adequate removal of debris from the site.

A second embodiment of the present invention avoids this limitation. The distal bearing has a first portion mounted to a first, fixed portion of the outer tube assembly, and a second portion mounted to a second, demountable portion of the outer tube assembly. To assemble the rotary abrader, the demountable portion of the outer tube is removed, the inner assembly with hub permanently attached is positioned within the fixed portion of the outer tube assembly, and the demountable portion of the outer assembly is remounted to the outer assembly. This construction has two advantages: the instrument can be easily disassembled for cleaning between uses, and the tubular portion of the inner assembly can have a larger diameter than the bearing so as to allow better transmission of torque and better aspiration of debris from the site.

Figure 29:
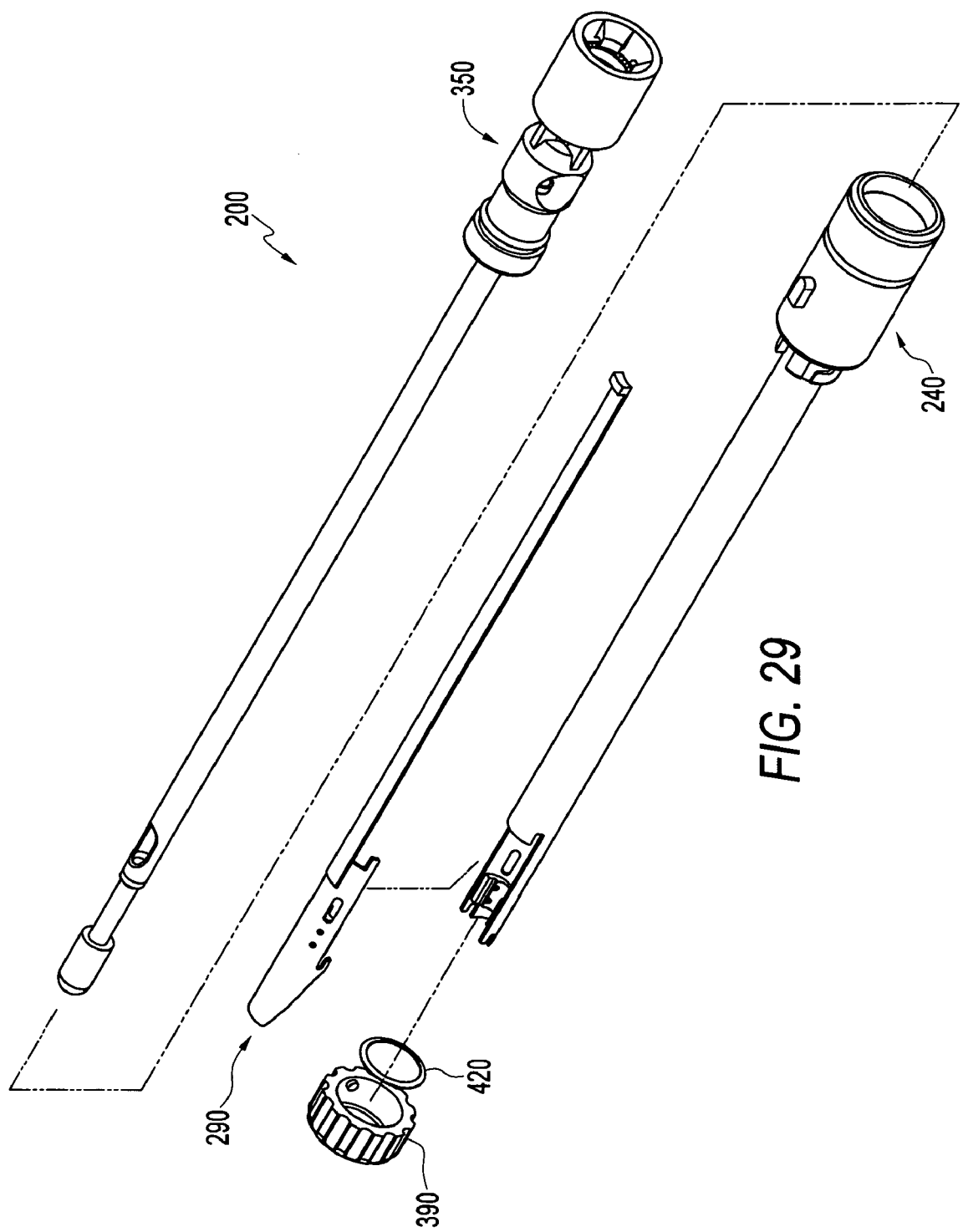
FIG. 29 is an exploded disassembled view of a rotary abrader constructed in accordance with a second embodiment of the invention.

Referring now to FIG. 29 showing an embodiment of the disclosed invention having a two-piece outer tubular assembly, rotary abrader 200 has an inner assembly 350, an outer assembly first portion 240, an outer assembly second portion 290, and a retainer 390 with spring washer 420.

Figure 30:
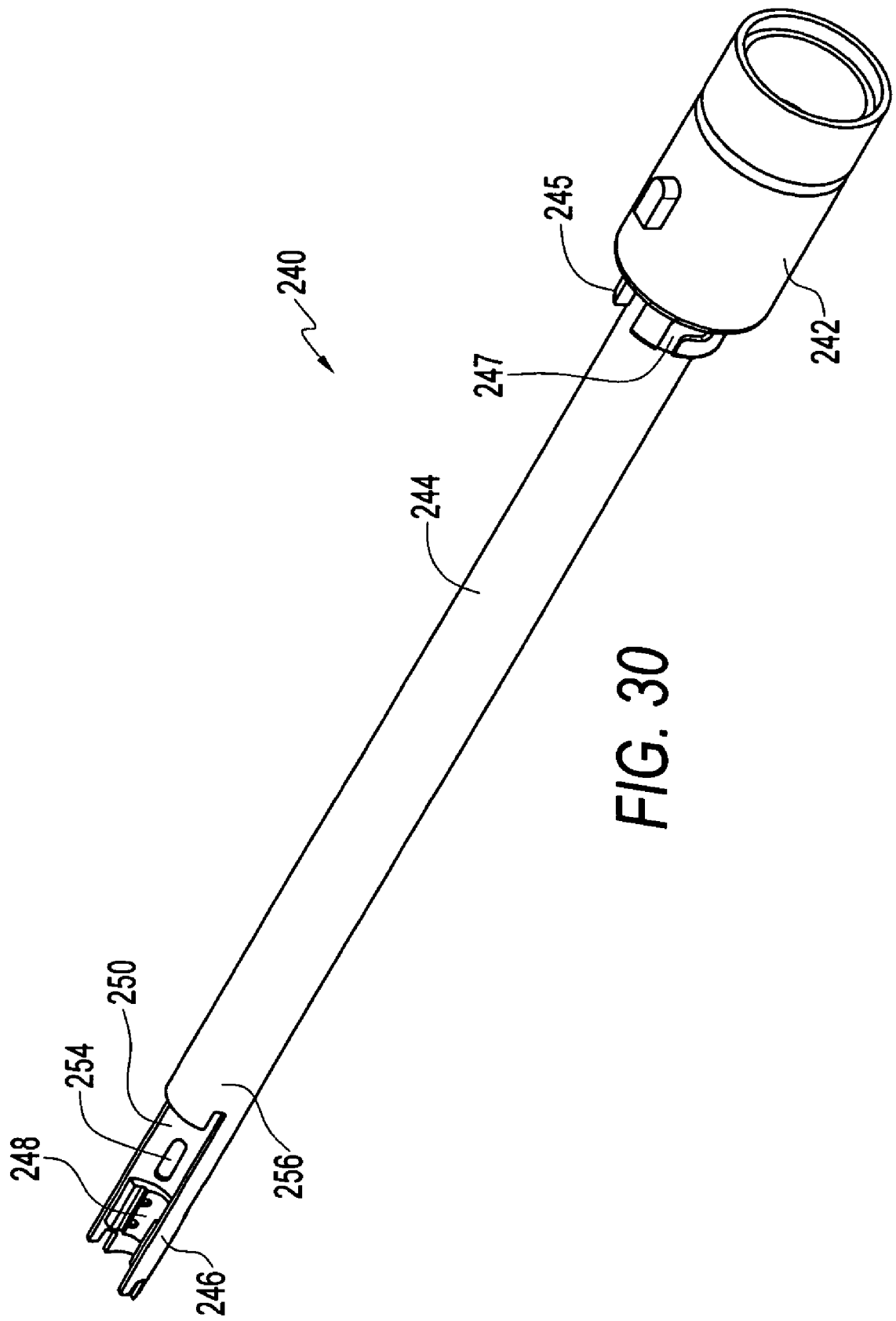
FIG. 30 is a perspective view of a first outer assembly of a rotary abrader constructed in accordance with a second embodiment of the invention.
Figure 31:
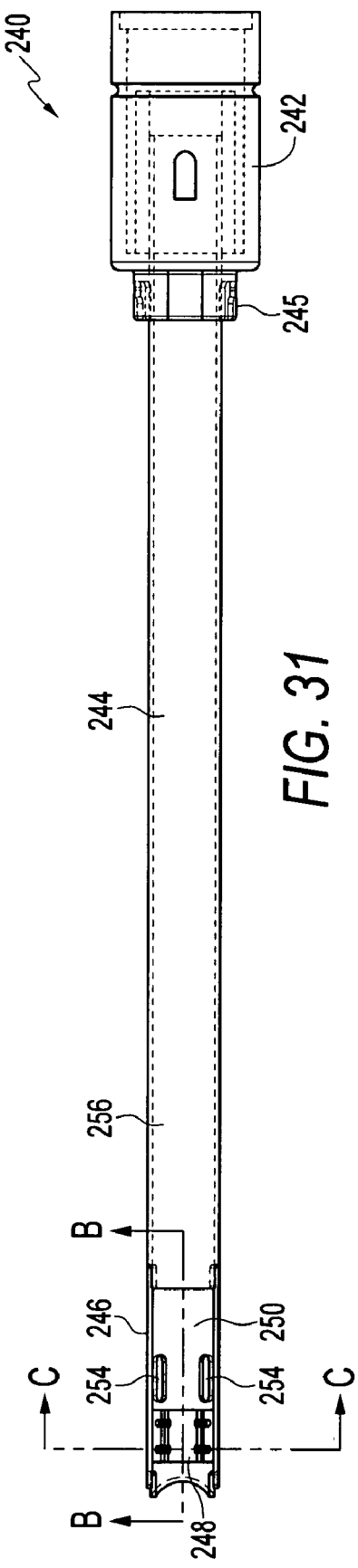
FIG. 31 is a plan view of the objects of FIG. 30.
Figure 32:
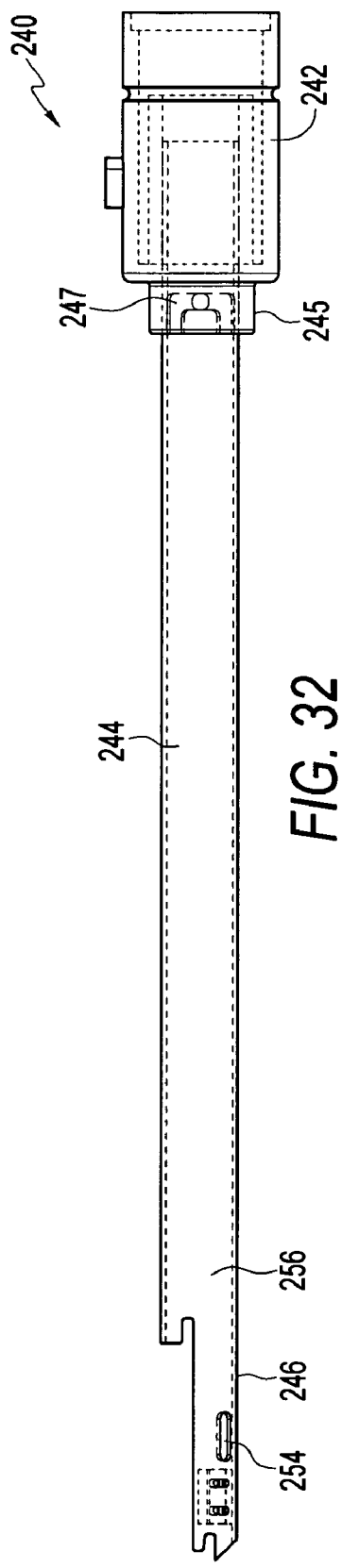
FIG. 32 is a side elevational view of the objects of FIG. 30.
Figure 33:
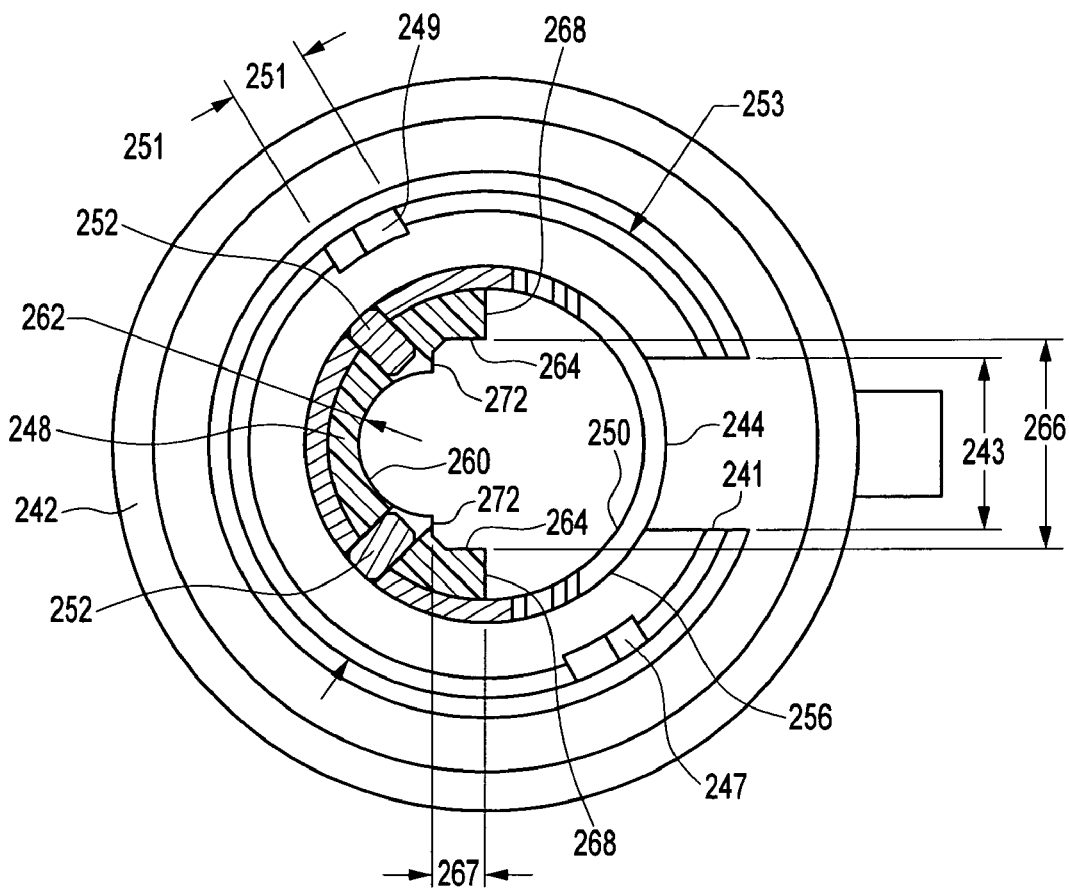
FIG. 33 is an expanded axial sectional view of the objects at location C-C of FIG. 31.
Figure 34:
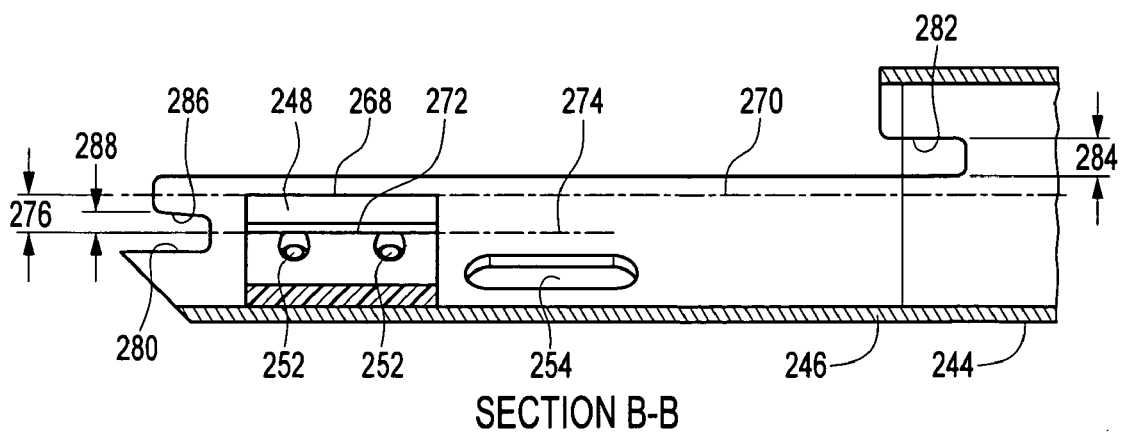
FIG. 34 is an expanded side elevational sectional view of the objects at location B-B of FIG. 31.
Figure 35:
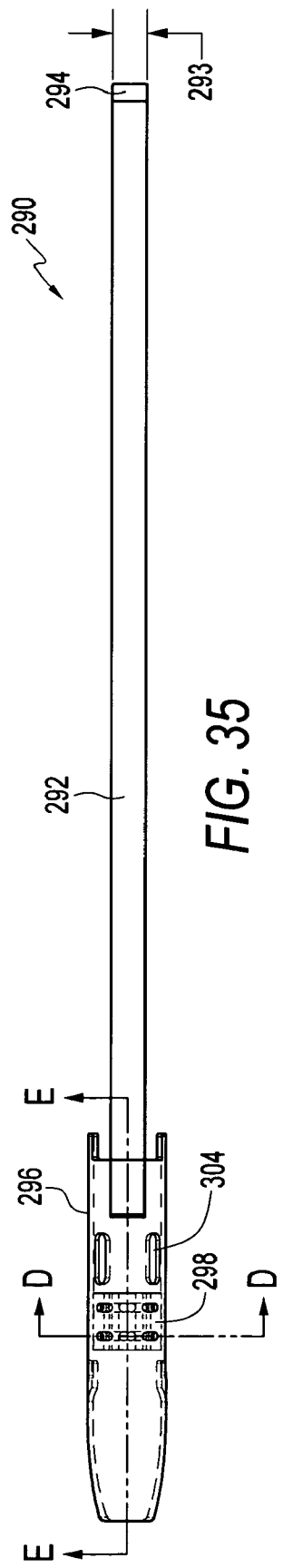
FIG. 35 is a plan view of a second outer assembly of a rotary abrader constructed in accordance with a second embodiment of the invention.
Figure 36:
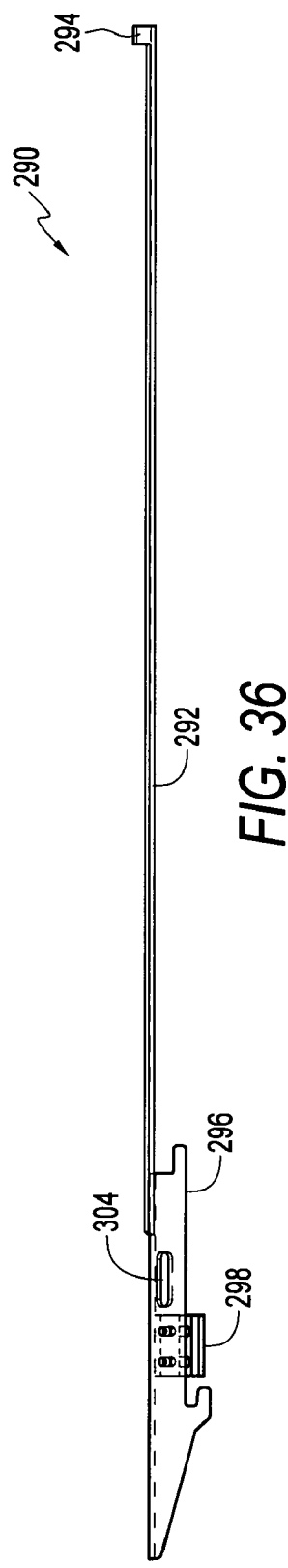
FIG. 36 is a side elevational view of the objects of FIG. 35.
Figure 37:
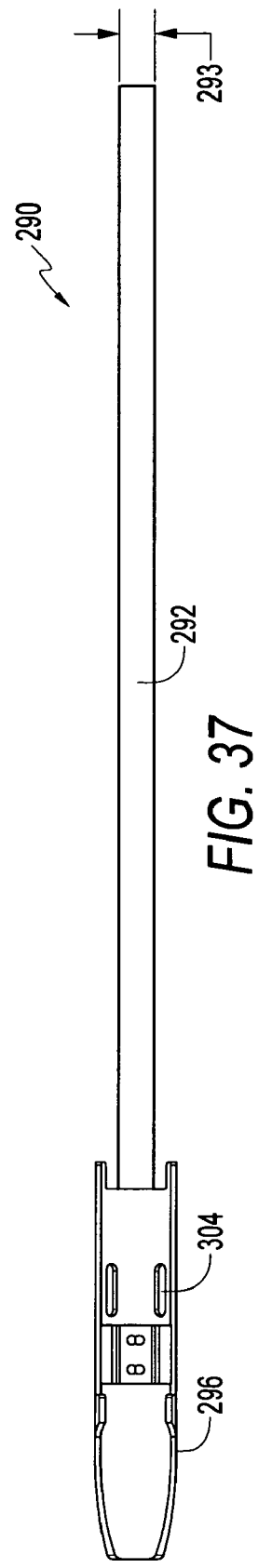
FIG. 37 is a bottom view of the objects of FIG. 35.
Figure 38:
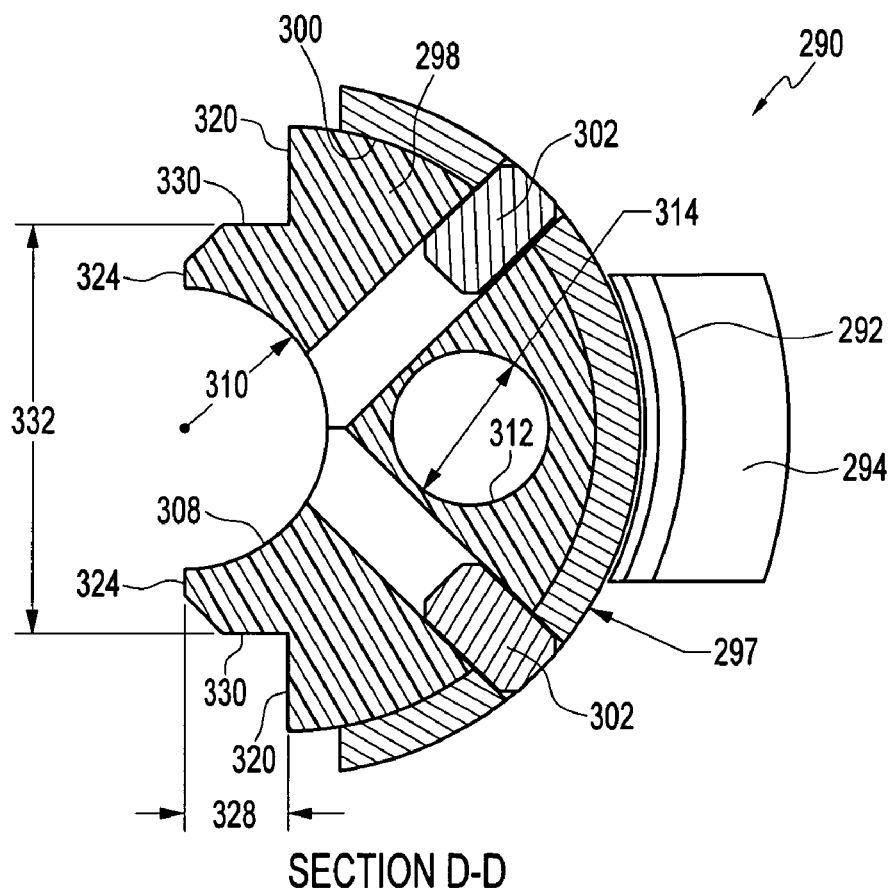
FIG. 38 is an expanded axial view of the objects at location D-D of FIG. 35.
Figure 39:
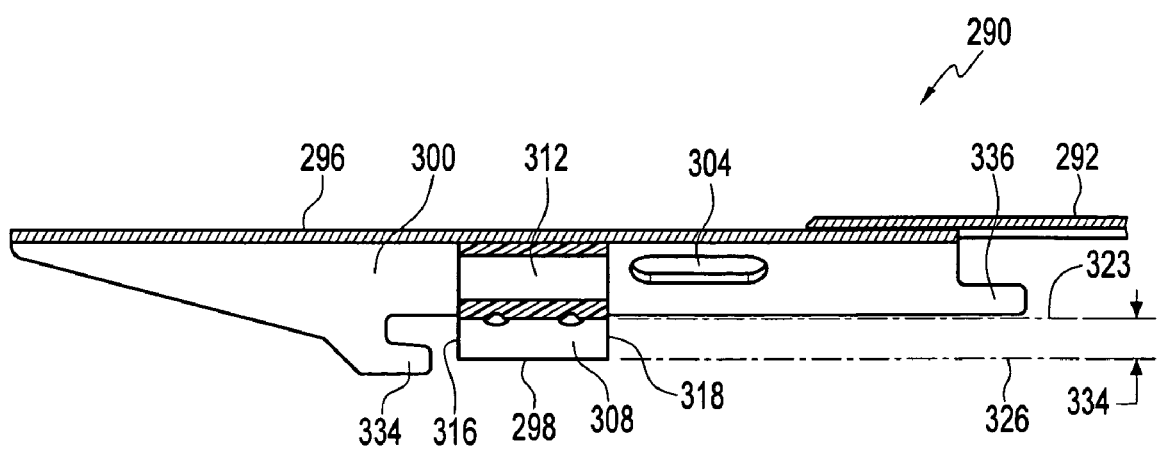
FIG. 39 is an expanded side elevational sectional view of the objects at location E-E of FIG. 35.
Figure 42:
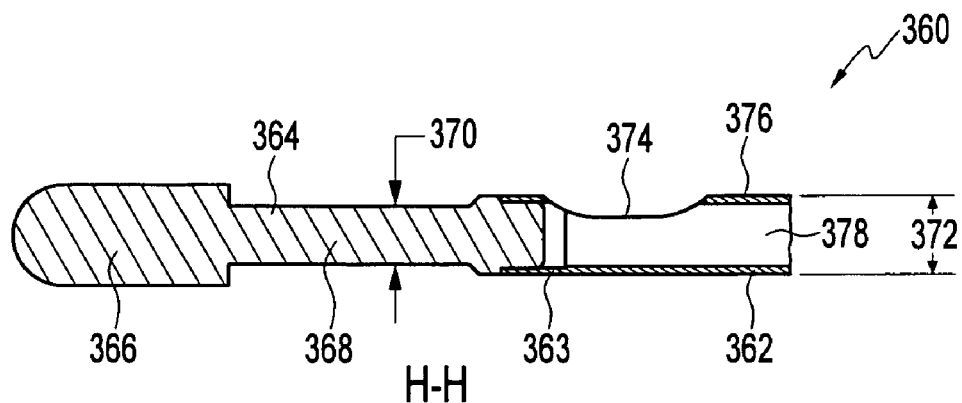
FIG. 42 is an expanded side elevational sectional view of the distal portion of the objects at location H-H of FIG. 40.
Figure 43:
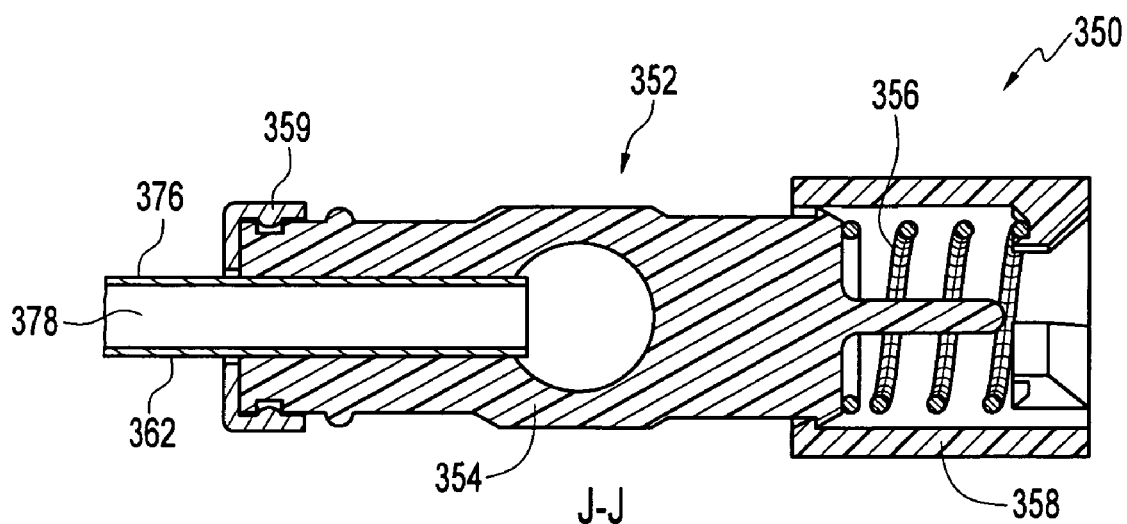
FIG. 43 is an expanded side elevational sectional view of the proximal portion of the objects at location J-J of FIG. 40.
Figure 44:
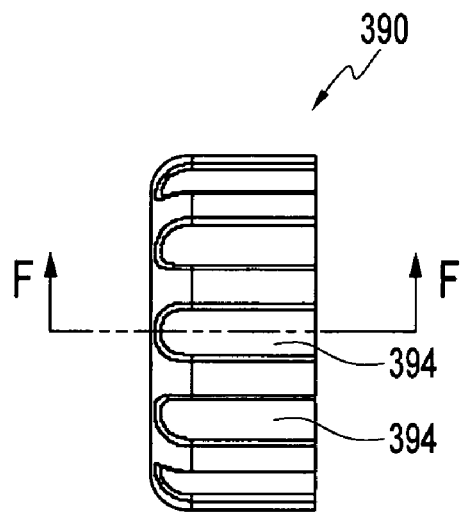
FIG. 44 is a side elevational view of the retainer of a rotary abrader constructed in accordance with a second embodiment of the invention.
Figure 45:
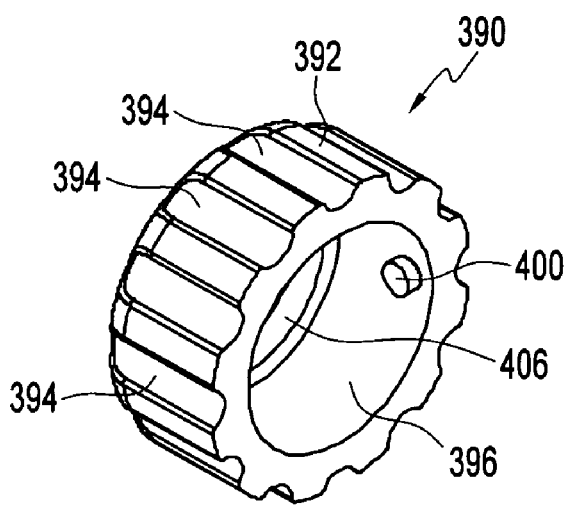
FIG. 45 is a perspective view of the object of FIG. 44.

As best seen in FIGS. 30 through 34, outer assembly first portion 240 has a proximal end forming a hub 242 suitable for removably mounting in a powered handpiece, and a tubular portion 244, hub 242 having a distal portion 245 of diameter 253. Distal end 245 has a first channel 241 of width 243 formed therein, the bottom surface of channel 241 being formed by tubular portion 244. Hub 242 also has in its distal end 245 second and third channels 247 and 249 of width 251 which have axial portions and circumferential portions. Tubular portion 244 has a distal end 246 with a first bearing portion 248 mounted to inner surface 250 of tubular portion 244 by pins 252. Elongated slots 254 extend from inner surface 250 to outer surface 256 of tubular portion 244. First bearing portion 248 has formed therein a first axial channel 260 having a semicircular cross-section of radius 262, and a second axial channel 264 of width 266 and depth 267. Surface 268 of bearing portion 248 is approximately coplanar with axis 270 of tubular portion 244. Surface 272 of bearing portion 248 forms the bottom of channel 264. Axis 274 of semicircular channel 260 is coplanar with surface 272. Depth 267 is approximately equal to the distance 276 between the axis of inner surface 250 of tubular portion 244, and the axis of first axial channel 260. As best seen in FIGS. 32 and 34, distal end 246 has formed therein a first slot 280 and a second slot 282, slot 282 being of a constant width 284. Slot 280 has an upper surface 286 inclined angle 288 from axis 270 of tubular portion 244.

Referring now to FIGS. 35 through 39, outer assembly second portion 290 has an elongated proximal portion 292 of width 293 having a flange 294 at its proximal end, width 293 being slightly less than width 243 of first slot 241 (FIG. 33), and a distal portion 296 formed to a cylindrical radius 297 with a second bearing portion 298 mounted to its inner surface 300 by pins 302, and elongated slots 304 extending from inner surface 300 to outer surface 306. Second bearing portion 298 has a channel 308 therein, channel 308 having a semicircular cross-section with a radius 310. Passage 312 of diameter 314 extends axially through bearing portion 298 from distal surface 316 to axial surface 318. Surfaces 320 of bearing portion 298 are coplanar with axis 323 of distal portion 296. Surface 324 is coplanar with the axis 326 of channel 308 and is parallel to surface 320 and displaced a distance 328. Parallel surfaces 330 are symmetrical about the plane containing axes 323 and 326, and are separated by distance 332 which is equal to distance 266 of first bearing portion 248 (FIG. 33). Distance 328 between surfaces 320 and 324 is equal to distance 267 between surfaces 268 and 272 of first bearing portion 248 (FIG. 33). Radius 310 of channel 308 is equal to radius 262 of channel 260 (FIG. 33). Distance 334 between axis 326 of channel 308 and axis 323 of distal portion 296 is equal to distance 276 between the axis of inner surface 250 of tubular portion 244 and the axis of axial channel 260 of first bearing portion 248 (FIG. 34). As best seen in FIG. 29, distal portion 296 has formed therein protrusions 334 and 336 which are in form complementary to slots 280 and 282 respectively.

Inner assembly 350 (shown in FIGS. 40 through 43) has a proximal end assembly 352 having an inner hub 354, spring 356, spring retainer 358, and thrust washer 359, together forming a means for transmitting rotary motion from a handpiece, and an elongated distal assembly 360 having a tubular portion 362 with a distal end member 364 affixed to distal end 363 by welding or another suitable means. Member 364 has a distal portion 366 forming an abrading element, and a cylindrical proximal portion 368, the diameter 370 of portion 368 being less than the outer diameter 372 of tubular portion 362. Aspiration port 374 extends from the outer surface 376 of tubular portion 362 to the inner lumen 378 near distal end 363.

Retainer 390 (FIGS. 44 through 47) forms a closed end tube having an outer cylindrical surface 392 with a plurality of grooves 394 formed therein, a cylindrical inner surface 396 of diameter 398 from which protrude radially cylindrical protrusions 400 of diameter 402. Diameter 402 is slightly less than width 250 of second channel 247 and third channel 249 of distal portion 245 of hub 242 (FIGS. 30 through 33). End wall 404 has formed therein axial cylindrical opening 406 of diameter 408, diameter 408 being slightly greater than diameter 253 of distal portion 245 of outer hub 242 (FIG. 33).

Figure 46:
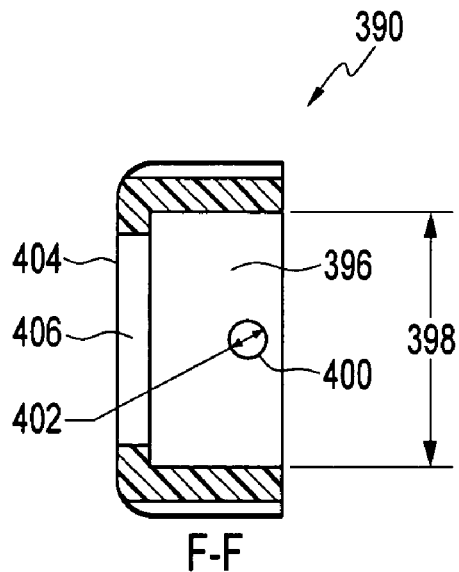
FIG. 46 is a side elevational sectional view of the object at location F-F of FIG. 44.
Figure 47:
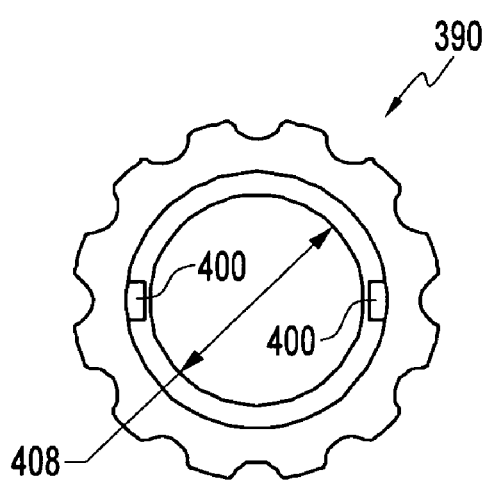
FIG. 47 is an axial end view of the object of FIG. 44.
Figure 48:
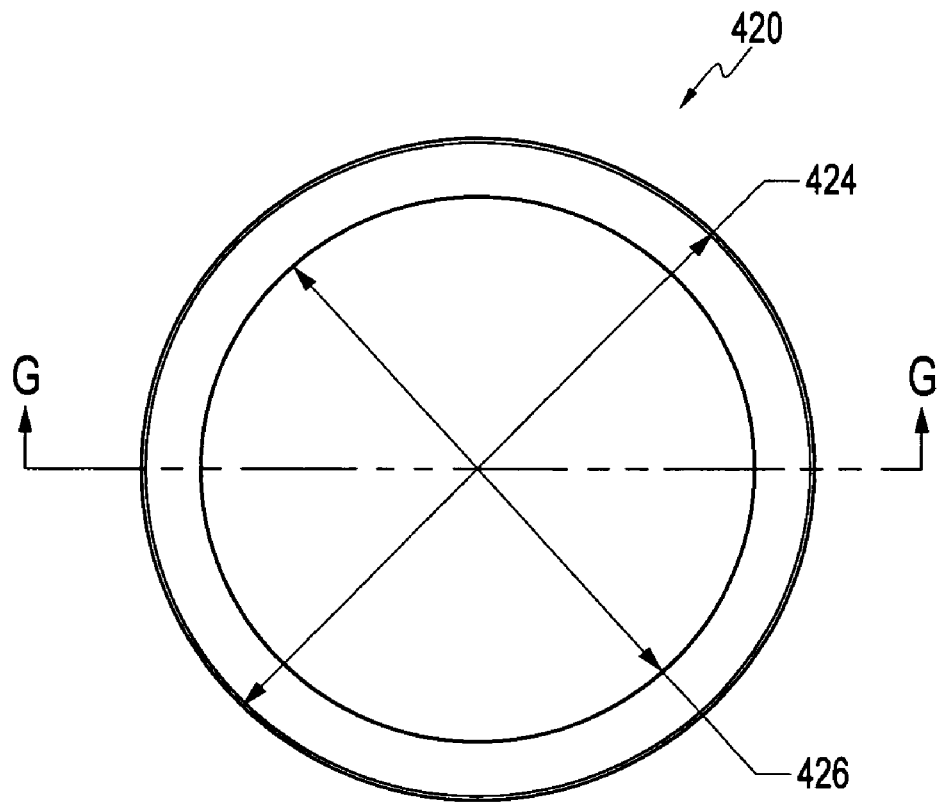
FIG. 48 is a plan view of the spring washer of a rotary abrader constructed in accordance with a second embodiment of the invention.
Figure 49:
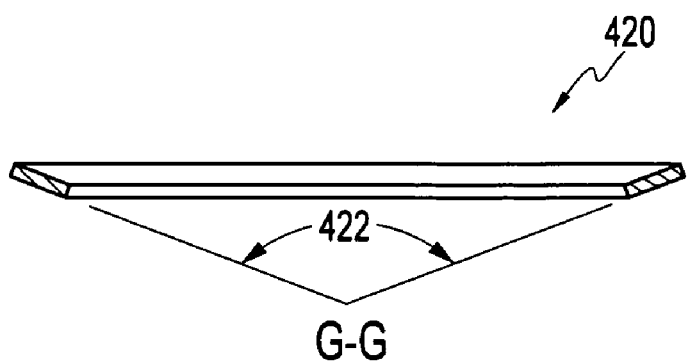
FIG. 49 is a side elevational sectional view of the object of FIG. 48.

Spring washer 420 (FIGS. 48 and 49) has a conical cross section with included angle 422, an outer diameter 424 and an inner diameter 426. Washer 420 is made from a high-yield strength spring material such as stainless steel. Outer diameter 424 is slightly less than diameter 398 of retainer 390, and inner diameter 426 is slightly greater than diameter 408 of retainer 390 (FIG. 46).

Figure 50:
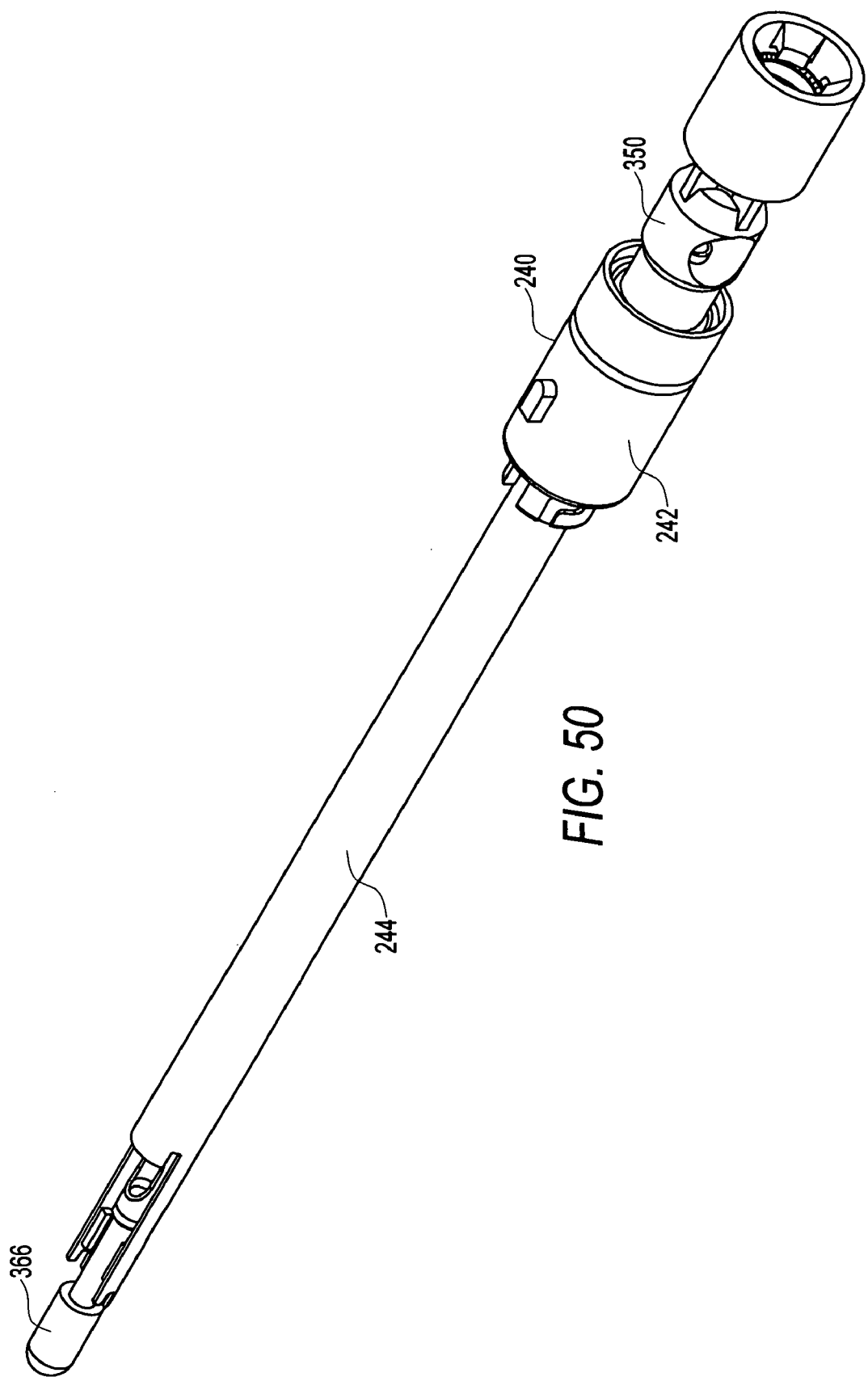
FIG. 50 is a perspective view of a partially assembled rotary abrader constructed in accordance with a second embodiment of the invention.
Figure 51:
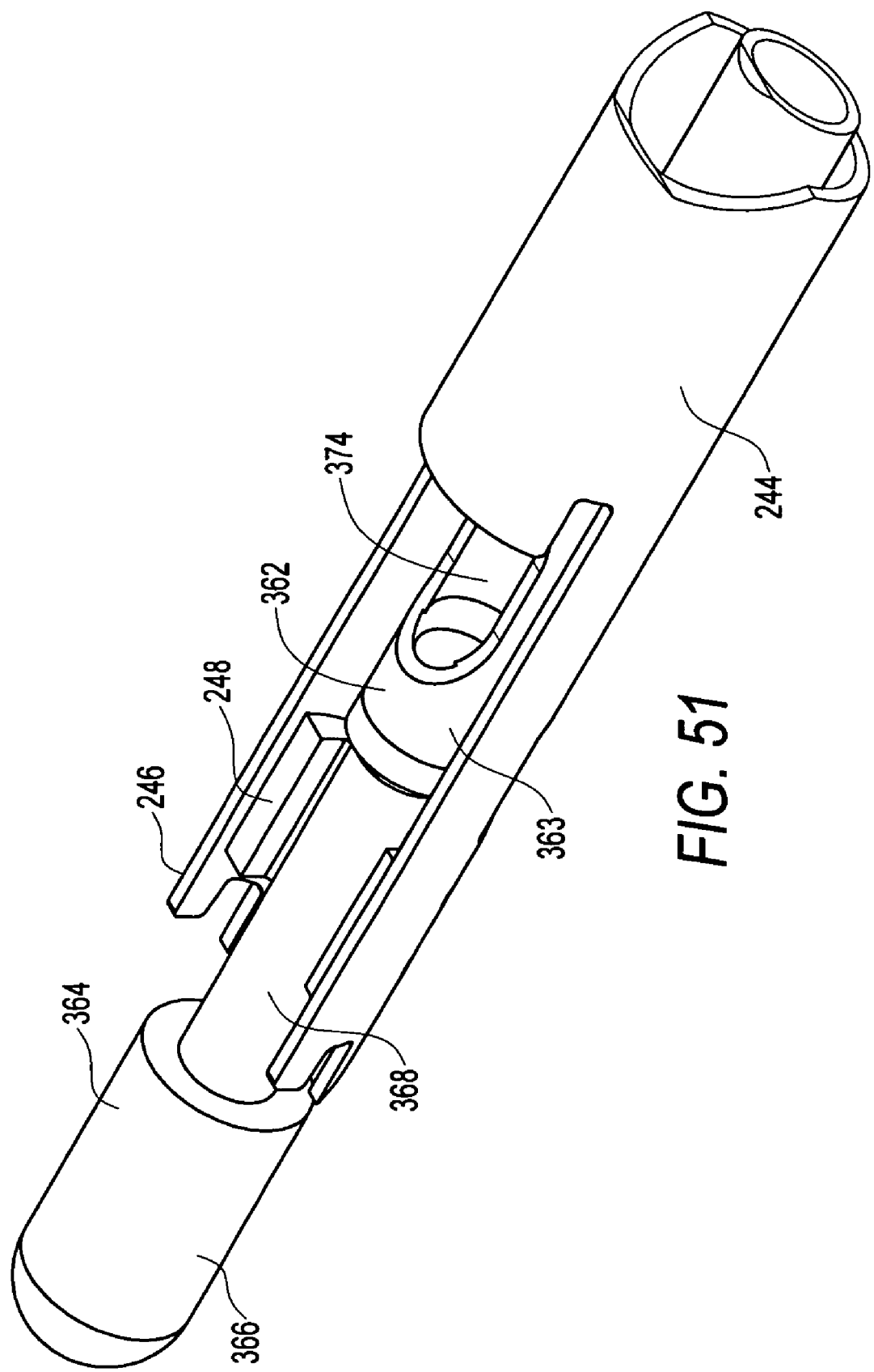
FIG. 51 is an expanded perspective view of the distal portion of the objects of FIG. 50.

Referring to FIGS. 50 and 51 showing a partially assembled abrader 200, inner assembly 350 is inserted into outer assembly first portion 240 from the proximal end. As best seen in FIG. 51, cylindrical portion 368 of member 364 is rotatably positioned within first channel 260 of first bearing portion 248 (FIG. 33).

Figure 54:
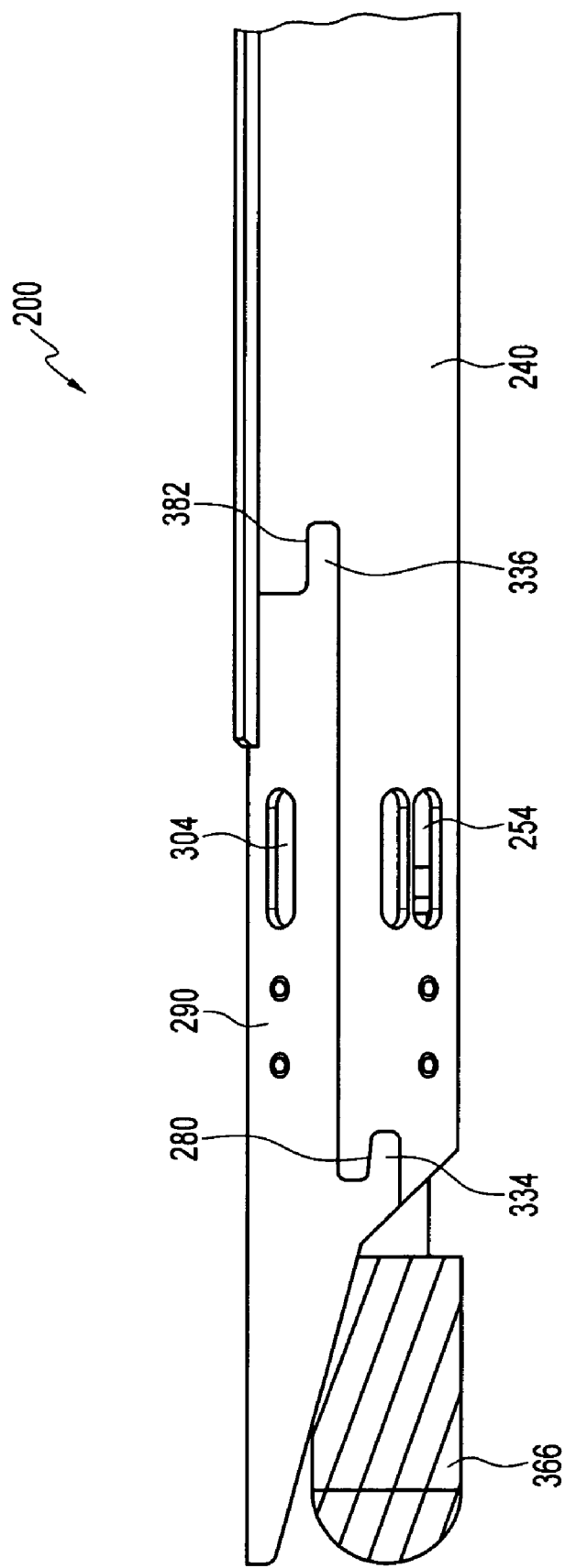
FIG. 54 is an expanded view of the distal portion of the objects of FIG. 53.
Figure 55:
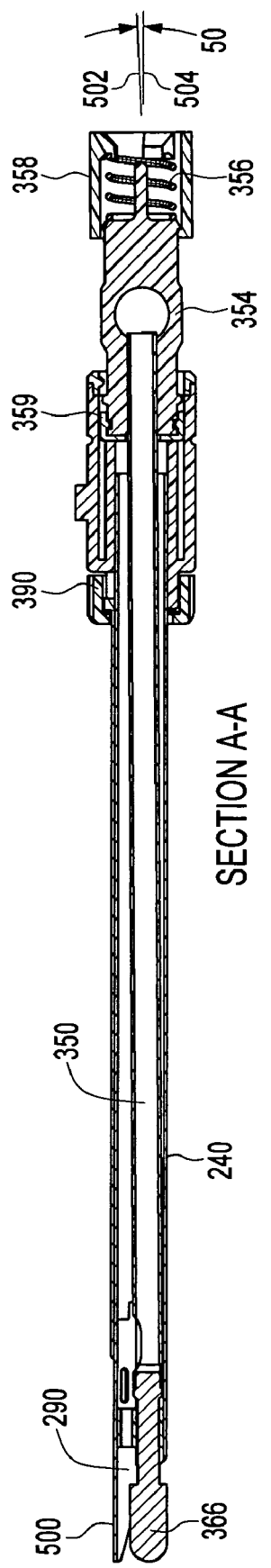
FIG. 55 is a side elevational sectional view of the objects of FIG. 52 along the axis of the abrader.
Figure 56:
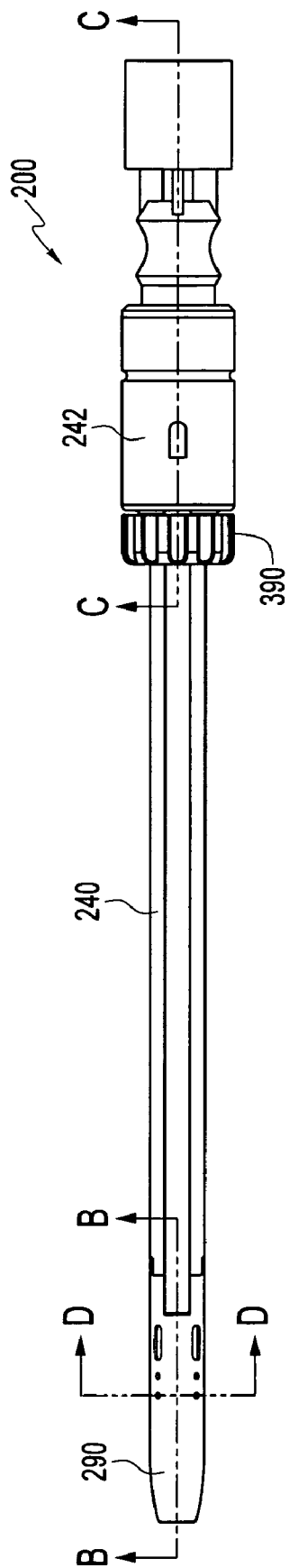
FIG. 56 is a plan view of the objects of FIG. 52.
Figure 57:
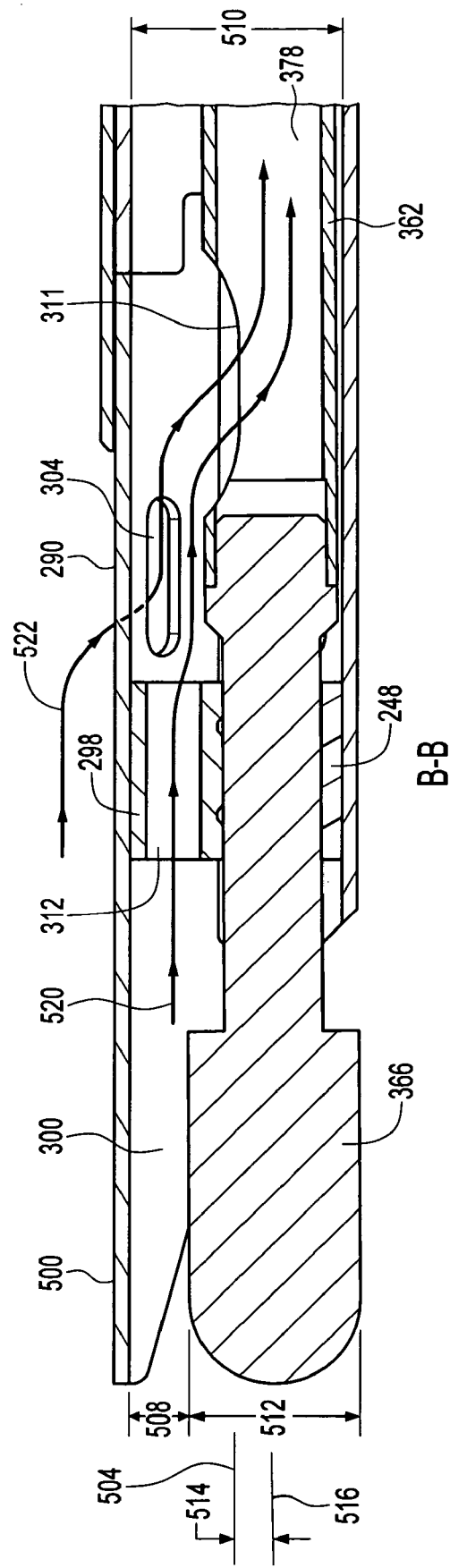
FIG. 57 is an expanded side elevational view of the distal portion of the objects at location C-C of FIG. 56.
Figure 58:
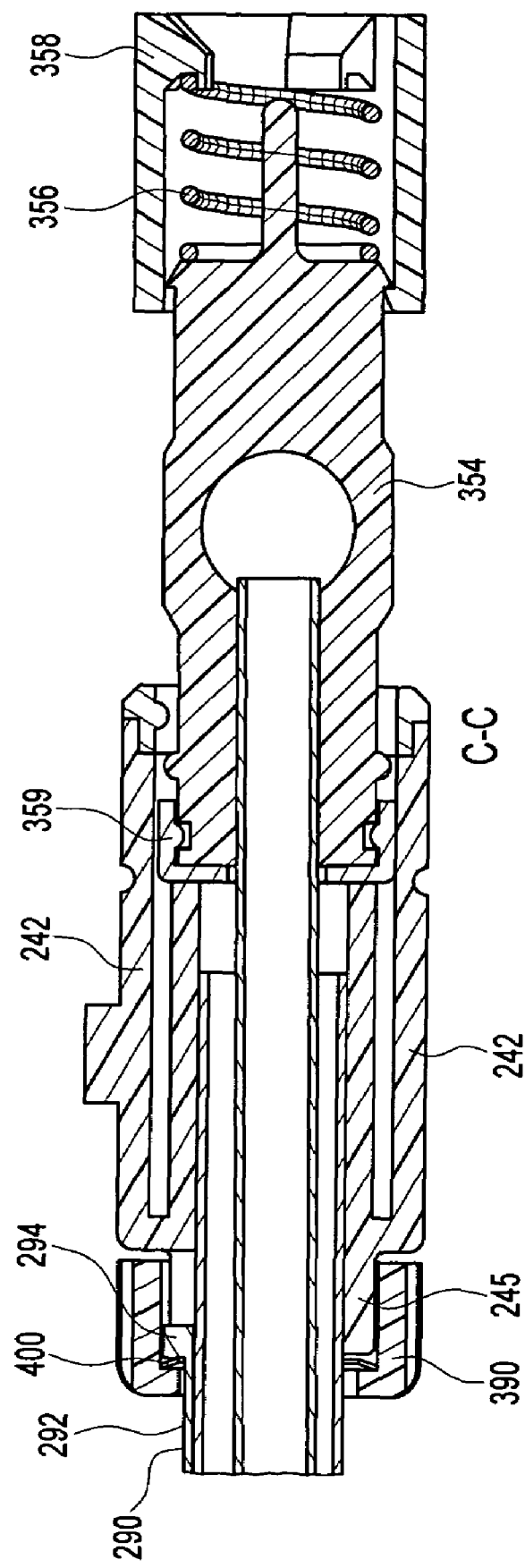
FIG. 58 is an expanded side elevational sectional view of the proximal portion of the objects at location C-C of FIG. 56.
Figure 59:
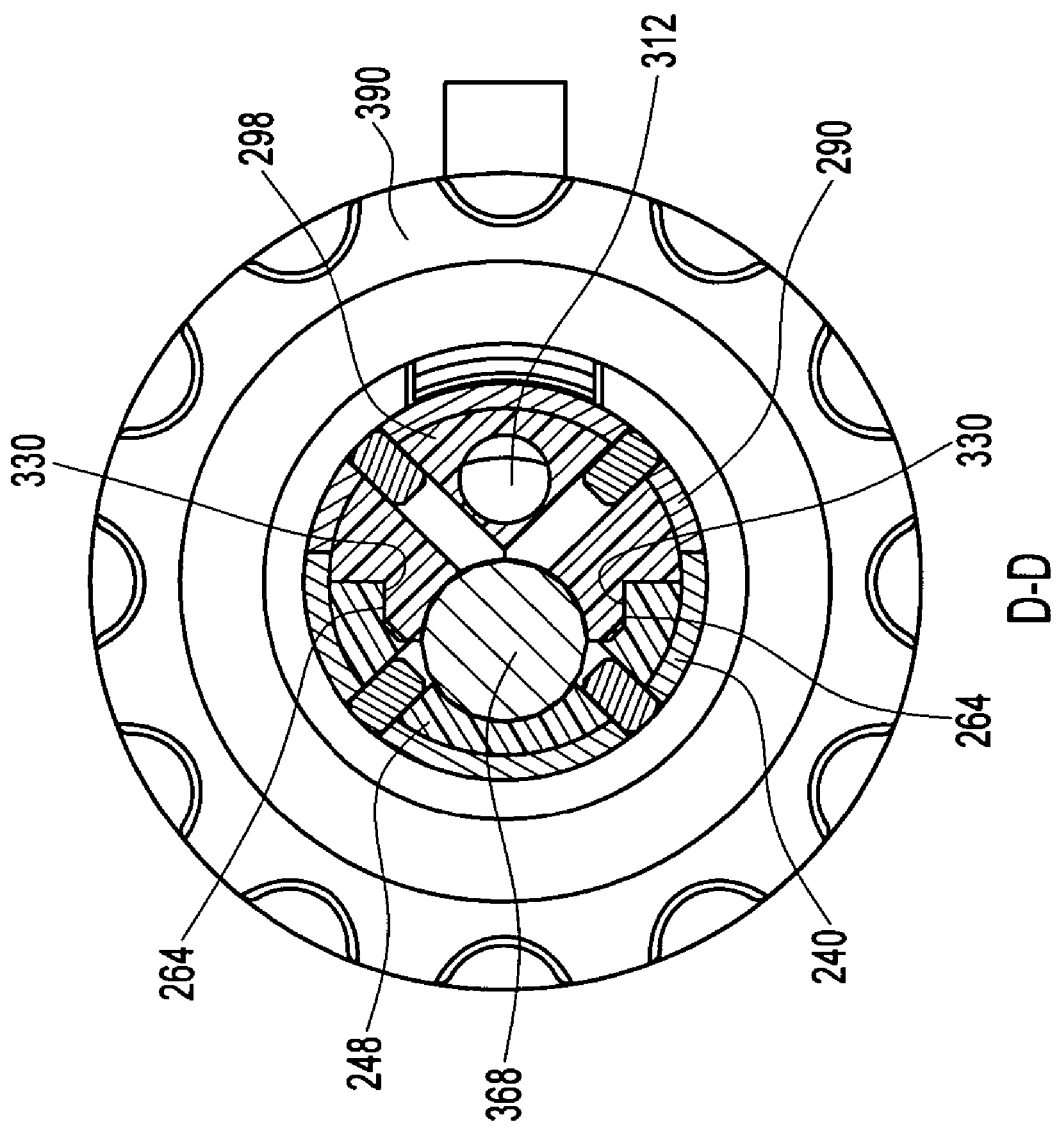
FIG. 59 is an expanded axial sectional view of the objects at location D-D of FIG. 56.
Figure 60:
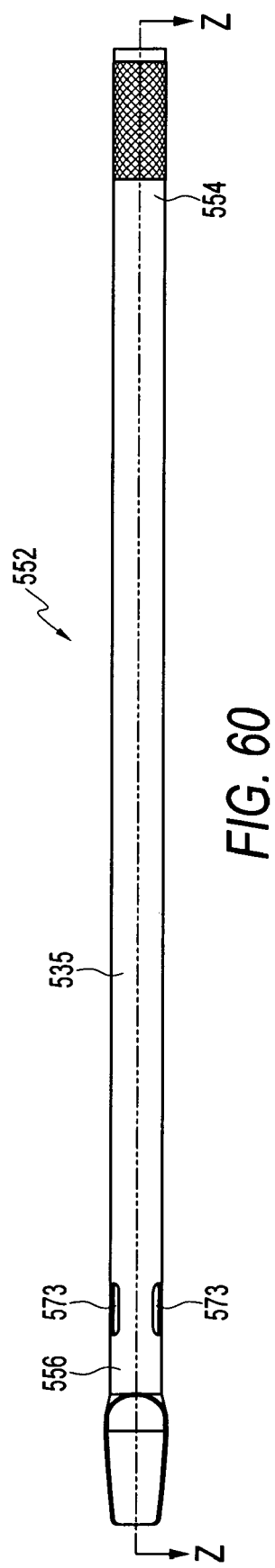
FIG. 60 is a plan view of the outer tube of a rotary abrader in accordance with a third embodiment of the invention.
Figure 61:
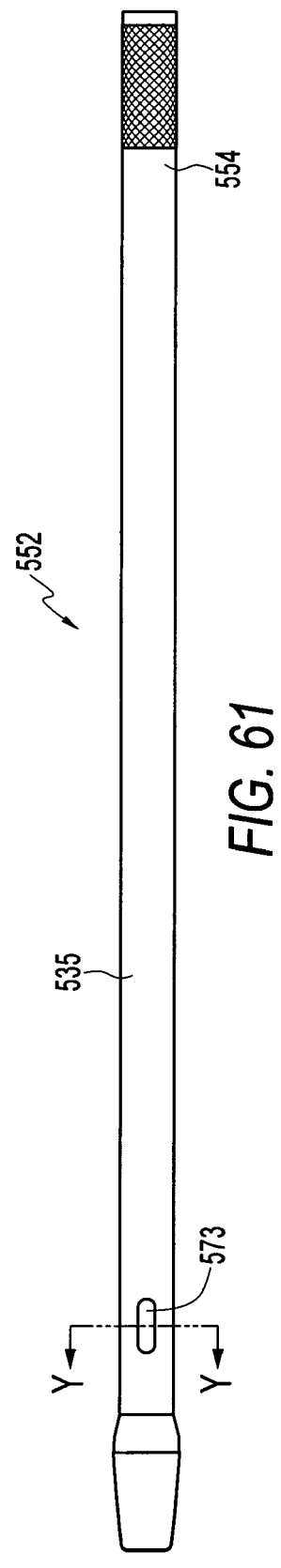
FIG. 61 is a plan view of the outer tube of a rotary abrader in accordance with a third embodiment of the invention.

When assembled, rotary abrader 200, shown in FIGS. 52 through 59, has second outer assembly 290 mounted to first outer assembly 240, with protrusions 334 and 336 engaging slots 280 and 282 respectively (FIG. 54). Distal end 500 of distal portion 296 of second outer assembly 290 forms a hood (guard) adjacent to abrading element 366. As best seen in FIG. 59, lateral alignment between the distal portions of first outer assembly 240 and second outer assembly 290 is established by surfaces 330 of second bearing portion 298 and channel 264 of first bearing portion 248. First channel 264 of first bearing portion 248 and first channel 308 of second bearing portion 298 together form a cylindrical bore in which cylindrical portion 368 of inner assembly 350 is rotatably positioned. As best seen in FIGS. 55 and 58, flange 294 of proximal portion 292 of second outer assembly 290 is constrained by retainer 390 so as to apply via spring washer 400 a proximal axial force to distal portion 296 of second outer assembly 290. Retainer 390 is removably attached to distal end 245 of hub 242 by engagement of protrusions 400 of retainer 390 (FIGS. 45 through 47) in second and third channels 247 and 249 of distal end 245 (FIGS. 30 through 32). As best seen in FIG. 55, axis 502 of inner assembly 350 is not parallel to axis 504 of the outer assembly, but is offset by angle 506. As best seen in FIG. 57, the clearance 508 between abrading element 366 and inner surface 300 of distal end 500 of second outer assembly 290 is equal to the difference between the inside diameter 510 of the outer assembly and the diameter 512 of abrading element 366 plus the distance 514 between the axis 516 of abrading element 366 and axis 504 of the outer assembly at the distal end.

The aspiration of debris from the site follows two paths. The first path 520 aspirates material from the region surrounding abrading element 366, through passage 312 in second bearing portion 298, and through aspiration port 311 to inner lumen 378 of tubular portion 362 of inner assembly 350. The second path 522 aspirates material from the region surrounding the distal end of abrader 200, through elongated slots 304, via aspiration port 311 to inner lumen 378 of tubular portion 362 of inner assembly 350.

Rotary abrader 200 is easily disassembled for cleaning. Because the distal bearing is split, the diameter of the mating surface on the inner member can be smaller than that of the proximal portion of the inner member or the abrading element. This allows the burr to be offset a greater distance than is possible in the previous embodiment. This greater offset provides enhanced visibility for the surgeon, and allows the use of a larger abrading element relative to the outer tube size while maintaining required minimum clearance between burr head and the hood.

In a third embodiment of the present invention, the elongated tubular portions of the inner and outer assemblies are concentric, rather than offset, but the burr head is enlarged. The hood is positioned at an angle and enlarged so that the required clearance can be maintained between the enlarged burr head and the hood. As in the previous embodiments, the larger diameter burr is preferably configured so that its cutting edge is aligned with the outer surface of the outer tube to provide a "flush cut."

Referring now to FIGS. 60 through 64, showing the outer tubular portion (outer tube) 552 of the outer assembly 550 of a rotary abrader formed in accordance with the third embodiment of the invention, outer tube 552 has a proximal end 554 and a distal end 556. Tube 552 has a lumen 553 of diameter 560 and an outer diameter 562. Distal end 56 has a first portion 564 of length 556 and a second portion 568 of length 570. Three elongated aspiration slots 573, at 120° apart, extend from the lumen 553 to tube outer surface 555. Beveled surfaces 575 and 577 together with outer surface 555 define a flared hood (or guard) 579.

Referring now to FIGS. 65 through 67, inner tube assembly 602 of a rotary abrader 660 constructed in accordance with the principles of the invention has an elongated tubular portion 604 with a proximal end 606 and a distal end 608. Distal end 608 has affixed thereto portion 610 having a proximal portion 612 of diameter 614 and a distal portion 616 forming an abrading element (or burr head) of diameter 617. Near distal end 608 of tubular portion 604 aspiration port 611 extends from lumen 612 to outer surface 613. A second aspiration port 619 is provided proximally on the inner tube 604, aligned with the three elongated aspiration slots 573 in the outer tube 552. Another variation is to have two aspiration ports 611 near the burr tip, 180° apart. Shrink tubing 618 is provided along the entire longitudinal length of the inner tube 604 and serves as a bearing between inner tube 604 and outer tube 552.

Figure 68:
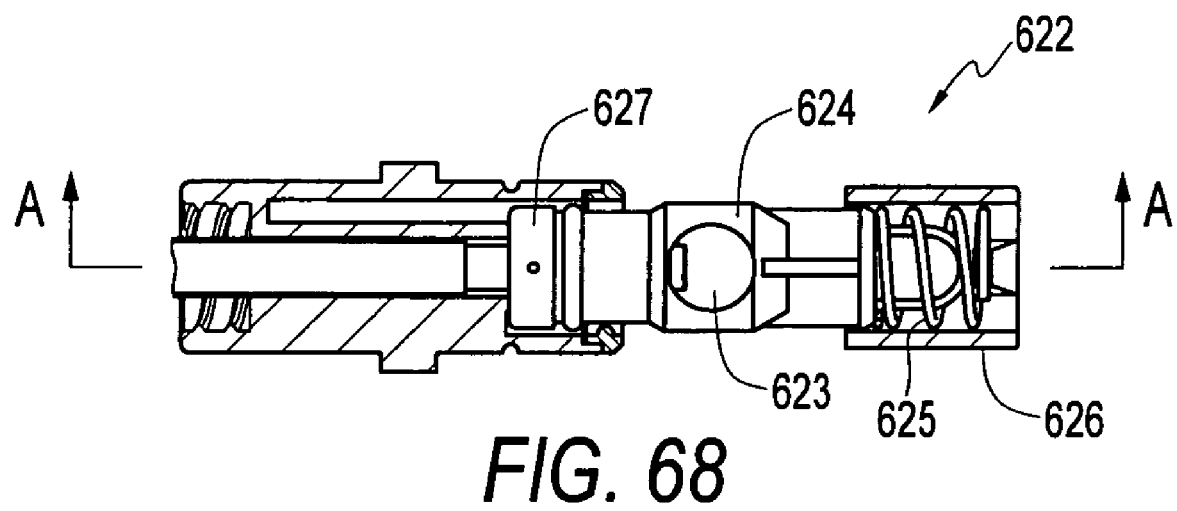
FIG. 68 is a plan sectional view of the proximal hub subassembly of the inner assembly of a rotary abrader constructed in accordance with a third embodiment of the invention.
Figure 69:
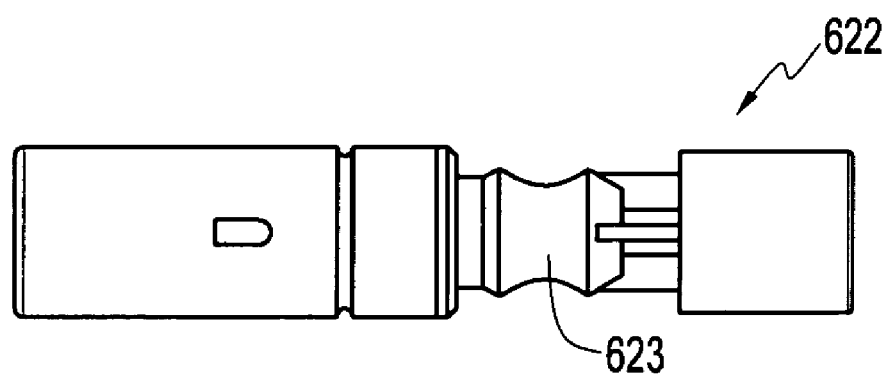
FIG. 69 is a side elevational view of the objects at location A-A of FIG. 19.

Referring now to FIGS. 68 through 69, showing inner hub assembly 622 as connected to abrader 660. Assembly 622 includes inner drive hub 624, spring 625, spring retainer 626 and thrust washer 627. Lateral passage 623 intersects bore 121.

Figure 70:
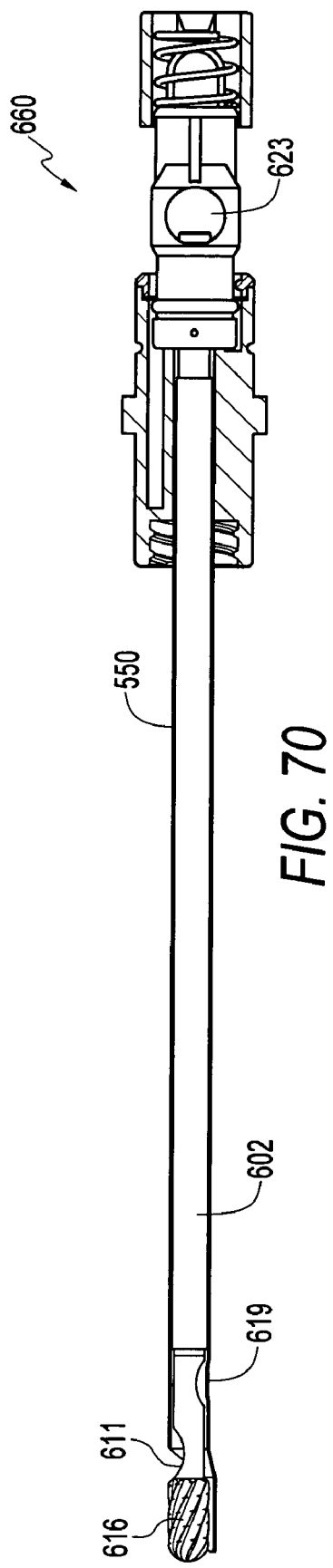
FIG. 70 side elevational sectional view of the rotary abrader of the third embodiment of the invention along the axis of FIG. 71.
Figure 71:
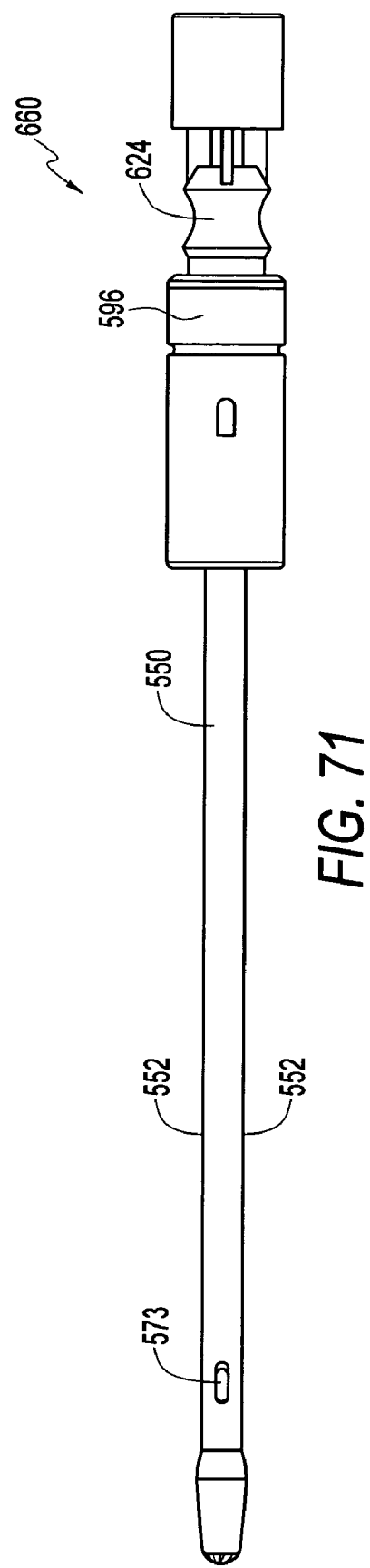
FIG. 71 plan view of the rotary abrader of the third embodiment of the invention.

Referring to FIGS. 70 and 71, rotary abrader 660, constructed in accordance with the principles of this invention, is assembled in the following manner. Tubular portion 604 of inner tube assembly 602 is inserted into distal end 556 of outer tube 552 of outer assembly 550. Hub assembly 622 of inner assembly 600 is inserted into proximal end 596 of outer assembly 550 such that proximal end 606 of tubular portion 604 of inner tube assembly 602 is positioned within inner hub 624 and slots 616 of tube 604 align axially and angularly with slots 628 of inner hub 624. The axis of the inner assembly 602 is coplanar with the axis of the outer assembly 550 while the radius of the hood 579 is enlarged as compared to the radius of the outer assembly 550 in order to accommodate a larger burr 616 while still maintaining the required minimum clearance and not obstructing the surgeon's view.

Debris is aspirated from the site along two paths which join in lumen 612 of inner tube 604, from which the debris is removed via opening 623 in inner hub 624 (see FIG. 26) by suction supplied by the handpiece. Debris in close proximity to burr head 616 follows a path along the hood 579 to aspiration port 611 in inner tube 604. Debris in the liquid in proximity to distal end 556 of outer tube 552 is aspirated via slots 573 to aspiration port 611 in inner tube 604.

Because the hood is enlarged as compared to the diameter of the outer assembly, the diameter of the abrading element can be increased and still maintain the minimum clearance required between the element and the hood. This allows the use of a larger abrading element for a given outer tube diameter than would be possible if the hood maintained the same radius. This larger diameter burr allows more rapid removal of bone than the smaller diameter burr of a conventional burr having the same outer tube diameter.

What is claimed as new and desired to be protected by Letters Patent of the United States is:

1. An apparatus for abrading tissue, comprising:
   an inner assembly including an inner tube rotatably positioned within an outer tube of an outer assembly;
   a hub formed at a proximal end of each of the inner assembly and the outer assembly;
   an abrading element located at a distal end of the inner tube of the inner assembly, wherein the cutting edge of the abrading element is aligned with the outer surface of the outer tube; and
   a hood located at a distal end of the outer tube of the outer assembly, wherein the inner tube and the outer tube are non-concentric and the inner tube is laterally and angularly offset along the entire length of the inner and outer tubes from the hood, so that a longitudinal axis of the inner tube is non-parallel to a longitudinal axis of the outer tube.

2. The apparatus of claim 1, wherein the hood is a distal extension of an outer surface of the outer tube and has two beveled edges.

3. The apparatus of claim 1, further comprising at least one aspiration port located near the distal end of the inner tube and extending from a lumen of the inner tube to an outer surface of the inner tube.

4. The apparatus of claim 3, further comprising a bearing located within the outer tube, the bearing comprising a cylindrical outer surface with grooves extending axially from a distal surface of the bearing to a proximal surface of the bearing.

5. The apparatus of claim 4, further comprising at least one slot in the outer tube of the outer assembly, the slot extending radially from the lumen of the outer tube to an outer surface of the outer tube.

6. The apparatus of claim 4, wherein debris may be aspirated through the grooves in the bearing and the at least one aspiration port into the lumen of the inner tube via suction.

7. The apparatus of claim 5, wherein debris may be aspirated through the at least one slot and aspiration port into the lumen of the inner tube via suction.

8. An apparatus for abrading tissue, comprising:
   an inner assembly including an inner tube rotatably positioned within an outer tube of an outer assembly, wherein the outer assembly has a fixed portion and a demountable portion;
   a hub formed at a proximal end of each of the inner assembly and the outer assembly, wherein the hub at the proximal end of the inner assembly is permanently affixed;
   an abrading element located at a distal end of the inner tube of the inner assembly, wherein the cutting edge of the abrading element is aligned with the outer surface of the outer tube; and
   a hood located at a distal end of the outer tube of the outer assembly, wherein the inner tube and the outer tube are non-concentric and the inner tube is laterally and angularly offset along the entire length of the inner and outer tubes from the hood, so that a longitudinal axis of the inner tube is non-parallel to a longitudinal axis of the outer tube.

9. The apparatus of claim 8, wherein the hood is a distal extension of an outer surface of the outer tube and has two beveled edges.

10. The apparatus of claim 8, further comprising at least one aspiration port located near the distal end of the inner tube and extending axially from a lumen of the inner tube to an outer surface of the inner tube.

11. The apparatus of claim 10, further comprising a bearing mounted within the outer tube, the bearing comprising channels extending axially from a distal surface of the bearing to a proximal surface of the bearing.

12. The apparatus of claim 11, further comprising at least one slot in the outer tube, the at least one slot extending radially from a lumen of the outer tube to an outer surface of the outer tube.

13. The apparatus of claim 11, wherein debris may be aspirated through the channels in the bearing and the at least one aspiration port into the lumen of the inner tube via suction.

14. The apparatus of claim 11, wherein debris may be aspirated through the at least one slot and aspiration port into the lumen of the inner tube via suction.

15. An apparatus for abrading tissue, comprising:
   an inner assembly including an inner tube rotatably positioned within an outer tube of an outer assembly, the outer assembly including an outer tube having a lumen with a radius;
   a hub formed at a proximal end of each of the inner assembly and the outer assembly;
   an abrading element located at a distal end of the inner tube, the abrading element having a radius that is greater than the radius of the lumen of the outer tube; and
   a hood located at a distal end of outer tube of the outer assembly, wherein the hood has a radius that is greater than a radius of the outer tube, wherein the inner tube and the outer tube are non-concentric and the inner tube is laterally and angularly offset along the entire length of the inner and outer tubes from the hood, so that a longitudinal axis of the inner tube is non-parallel to a longitudinal axis of the outer tube.

16. The apparatus of claim 15, further comprising at least one aspiration port, located near the distal end of the inner tube and extending axially from a lumen of the inner tube to an outer surface of the inner tube.

17. The apparatus of claim 15, further comprising at least one slot in the outer tube of the outer assembly, the slot extending radially from a lumen of the outer tube to an outer surface of the outer tube.

18. The apparatus of claim 15, wherein debris may be aspirated through the at least one aspiration port into the lumen of the inner tube via suction.

19. The apparatus of claim 16, wherein debris may be aspirated through the at least one slot and aspiration port into the lumen of the inner tube via suction.

20. The apparatus of claim 15, wherein the abrading element has a cutting edge that is aligned with an outer surface of the outer tube.

* * * * *